Figure 1:
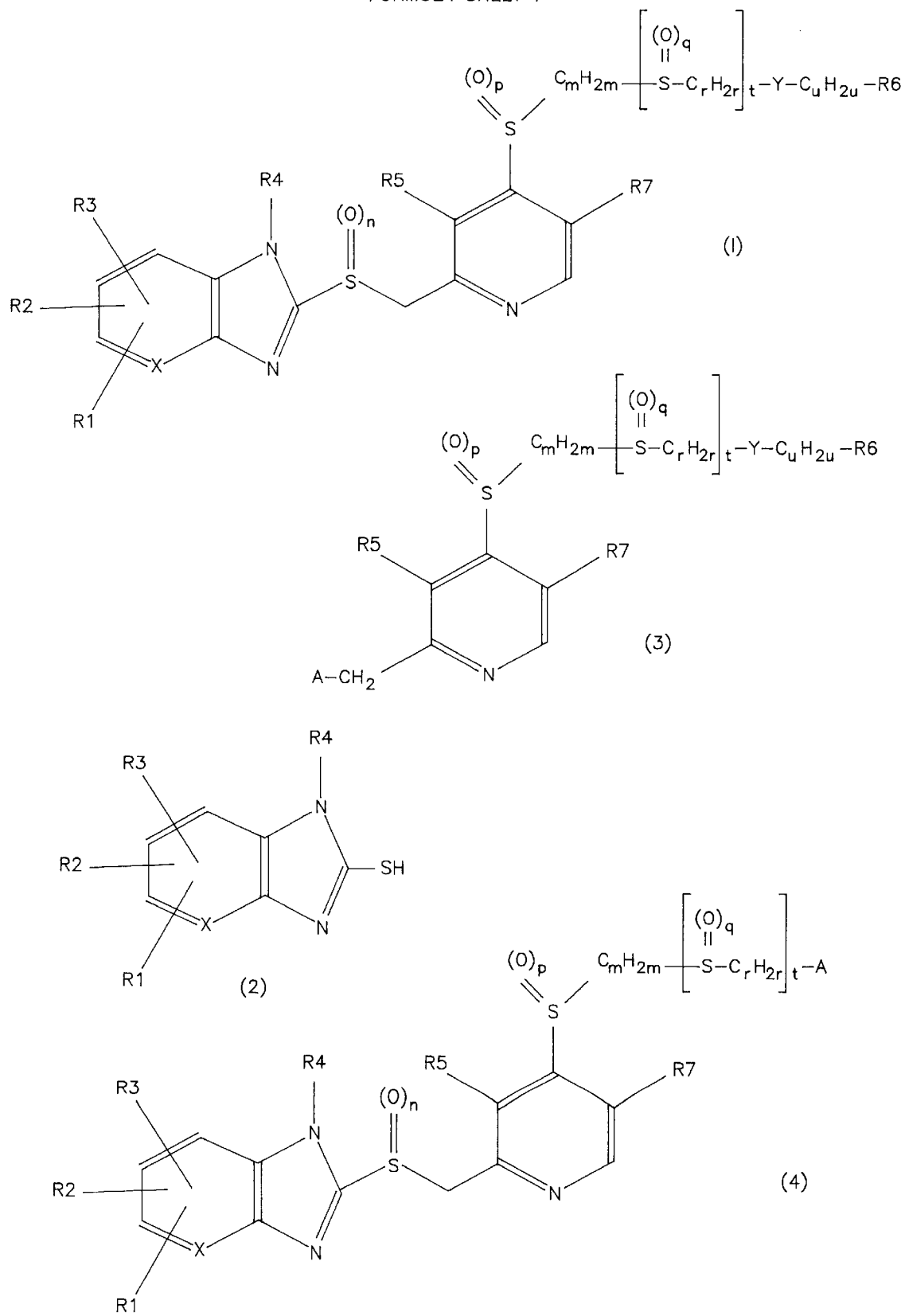
Figure 2:
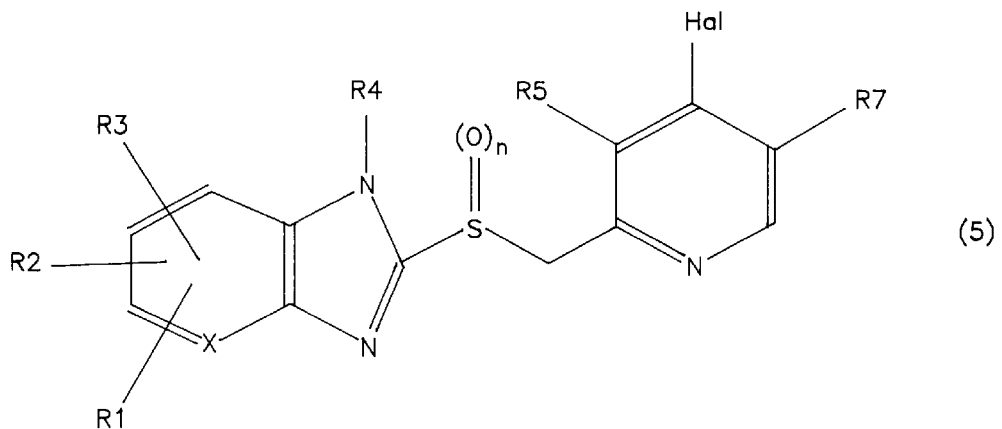
Figure 2:
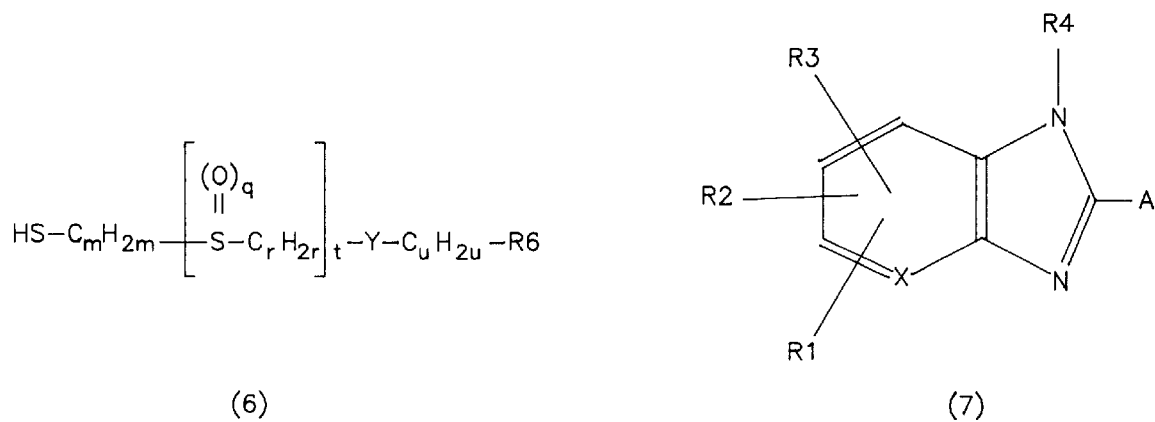
Figure 2:
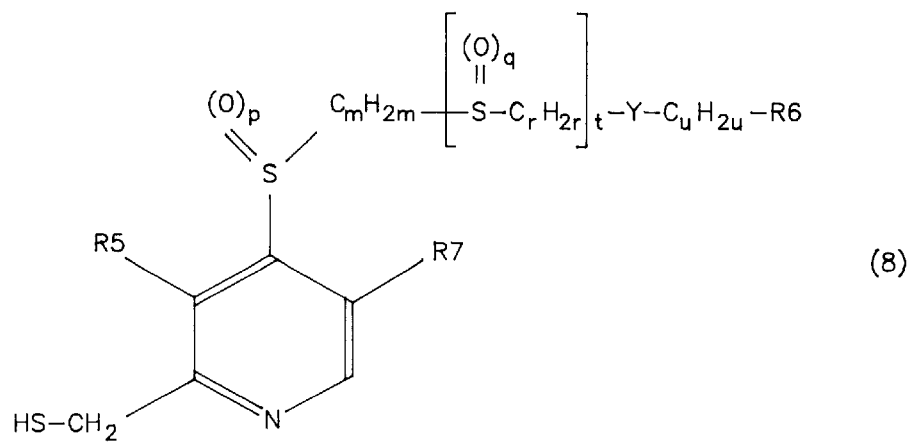

United States Patent

Kohl et al.

[11] Patent Number: 5,859,030
[45] Date of Patent: Jan. 12, 1999

[54] SUBSTITUTED ARYLALKYLTHIOALKYLTHIOPYRIDINES FOR USE IN THE CONTROL OF HELICOBACTER BACTERIA

[75] Inventors: Bernhard Kohl; Gerhard Grundler; Jörg Senn-Bilfinger, all of Constance, Germany

[73] Assignee: BYK Gulden Lomberg Chemische Fabrik GmbH, Constance, Germany

[21] Appl. No.: 750,785

[22] PCT Filed: Jun. 9, 1995

[86] PCT No.: PCT/EP95/02237

§ 371 Date: Apr. 10, 1997

§ 102(e) Date: Apr. 10, 1997

[87] PCT Pub. No.: WO95/34554

PCT Pub. Date: Dec. 21, 1995

[30] Foreign Application Priority Data

Jun. 10, 1994 [CH] Switzerland ............ 1845/94

[51] Int. Cl.⁶ ............. C07D 401/12; A61K 31/415
[52] U.S. Cl. ............ 514/338; 514/303; 514/242; 514/269; 514/333; 546/273.7; 546/272.4; 546/256; 546/269.7; 546/193; 544/333; 544/182
[58] Field of Search ............ 514/338, 303, 514/242, 269, 333; 546/273.7, 272.4, 256, 269.7, 193; 544/333, 182

[56] References Cited

U.S. PATENT DOCUMENTS 4,387,225  6/1983  Douglas et al. .......... 544/212
4,450,165  5/1984  Araki et al. ............. 424/258
4,560,693  12/1985 Rainer .................... 514/338
5,504,082  4/1996  Kawakita et al. ......... 514/218
5,587,389  12/1996 Kohl et al. .............. 514/338
5,668,131  9/1997  Senn-Bilfinger ......... 514/234.5

FOREIGN PATENT DOCUMENTS 1234058  6/1971  United Kingdom.

*Primary Examiner*—Jane Fan
*Attorney, Agent, or Firm*—Jacobson, Price, Holman & Stern, PLLC

[57] ABSTRACT

A compound of the formula I

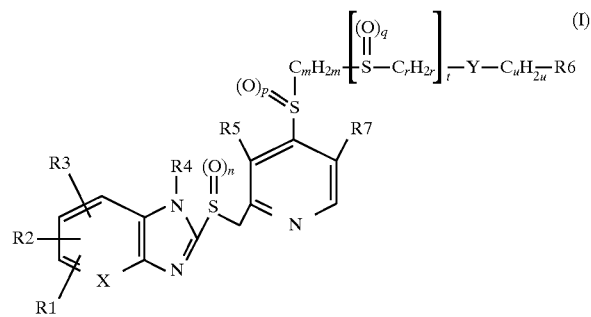

Wherein all the variables are defined in the specification. The compounds are used for controlling Helicobacter bacteria.

18 Claims, 2 Drawing Sheets

FORMULA SHEET I

FORMULA SHEET II (5)

(6)　　　　(7)

(8)

SUBSTITUTED ARYLALKYLTHIOALKYLTHIOPYRIDINES FOR USE IN THE CONTROL OF HELICOBACTER BACTERIA

This application is a 371 of PCT/EP95/02237, Jun. 9, 1995, now WO95/34554, Dec. 21, 1995.

APPLICATION AREA OF THE INVENTION

The invention relates to compounds which are intended to be used in the pharmaceutical industry as active compounds for the production of medicaments.

KNOWN TECHNICAL BACKGROUND

European Patent Application 150 586 discloses 2-(pyridylmethylthio- or -sulfinyl) benzimidazoles which can be substituted in the pyridine moiety of the molecule in the 4-position, inter alia, by alkylthio or arylthio radicals. A long-lasting inhibition of gastric acid secretion is indicated for the compounds described. - International Patent Application WO089/038-30 describes that the same, and other structurally similar compounds should be suitable for the treatment of osteoporosis. - International Patent Application WO92/12976 describes specifically substituted 2-(pyridylmethylthio- or -sulfinyl)-benzimidazoles which should be active against Helicobacter bacteria and for which it is furthermore disclosed that they should be suitable for the prevention and treatment of a whole series of disorders of the stomach. International Patent Application WO93/24480 describes other specifically substituted 2-(pyridylmethylthio- or -sulfinyl) -benzimidazoles which should be active against Helicobacter bacteria.

DESCRIPTION OF THE INVENTION

The invention relates to compounds of the formula I (see attached formula sheet I) in which X is CH or N, Y is S, SO, $SO_2$, O, NH or N-1-4C-alkyl, R1 is hydrogen, 1-4C-alkyl, 1-4C-alkoxy or halogen, R2 is hydrogen, 1-4C-alkyl, 1-4C-alkoxy, halogen, trifluoromethyl, completely or predominantly fluorine -substituted 1-4C-alkoxy, chlorodifluoromenth-oxy, 2-chloro-1,1,2-trifluoroethoxy or together with R3, if desired, completely or partially fluorine -substituted 1-2C-alkylenedioxy or chlorotrifluoroethylenedioxy, R3 is hydrogen, completely or predominantly fluorine substituted 1-4C-alkoxy, chlorodifluoromethoxy, 2-chloro-1,1,2-trifluoroethoxy or together with R2, if desired, completely or partially fluorine substituted 1-2C-alkylenedioxy or chlorotrifluoroethylenedioxy, R4 is hydrogen, 1-4C-alkyl, R14-substituted 1-4C-alkyl, 1-4C-alkylcarbonyl, 2-4C-alkenylcarbonyl, halo-1-4C-alkylcarbonyl, N(R15)R16-1-4C-alkylcarbonyl, di-1-4C-alkylcarbamoyl or 1-4C-alkylsulfonyl, R5 is hydrogen, 1-4C-alkyl or 1-4C-alkoxy, R6 is a mono- or di-1-4C-alkylcarbamoyl or -thio carbamoyl radical, an N-1-4C-alkyl-N'-cyanoamidino radical, a 1-N-1-4C-alkylamino-2-nitroethylene radical, an N-2-propynyl-N'-cyanoamidino radical, an aminosulfonylamidino radical, or an R8- and R9-substituted cyclic system or bicyclic system which is selected from the group consisting of benzene, furan, thiophene, pyrrole, oxazole, isoxazole, thiazole, thiazoline, isothiazole, imidazole, imidazoline, pyrazole, triazole, tetrazole, thiadiazole, thiadiazole-1-oxide, oxadiazole, pyridine, pyridine-N-oxide, pyrimidine, triazine, pyridone, benzimidazole, imidazopyridine, benzothiazole and benzoxazole, R7 is hydrogen, 1-4C-alkyl or 1-4C-alkoxy, R8 is hydrogen, 1-4C-alkyl, hydroxyl, 1-4C-alkoxy, halogen, nitro, guanidino, carboxyl, 1-4C-alkoxycarbonyl, R10-substituted 1-4C-alkyl or -N(Rll)R12, R9 is hydrogen, 1-4C-alkyl, hydroxyl, 1-4C-alkoxy, fluorine or trifluoromethyl, R10 is hydroxyl,-1-4C-alkoxy, carboxyl, 1-4C-alkoxycarbonyl or -N(R11)R12, where R11 is hydrogen, 1-4C-alkyl or —CO—R13 and R12 is hydrogen or 1-4C-alkyl, or where R11 and R12, together and including the nitrogen atom to which both are bonded, are a piperidino or morpholino radical, R13 is hydrogen, 1-4C-alkyl or 1-4C-alkoxy, R14 is hydroxyl, 1-4C-alkoxy, carboxyl, 1-4C-alkoxycarbonyl or —N(R15)R16, where R15 is 1-4C-alkyl and R16 is 1-4C-alkyl, or where R15 and R16, together and including the nitrogen atom to which both are bonded, are a piperidino or morpholino radical, m is a number from 2 to 7, n is the number 0 or 1, p is the number 0 or 1, q is the number 0, 1 or 2, r is a number from 2 to 7, t is the number 0 or 1 and u is a number from 0 to 7 and their salts those compounds of the formula I being excluded in which Y is S or SO and, at the same time, X is CH, t is the number 0, u is the number 0, R4 is hydrogen or 1-4C-alkyl and R6 is an R8- and R9-substituted cyclic system or bicyclic system which is selected from the group consisting of benzene, furan, thiophene, pyrrole, oxazole, isoxazole, thiazole, thiazoline, isothiazole, imidazole, imidazoline, pyrazole, triazole, tetrazole, thiadiazole, oxadiazole, pyridine, pyridine-N-oxide, pyrimidine and benzimidazole, and furthermore those compounds of the formula I being excluded in which Y is NH or N-1-4C-alkyl and, at the same time, t is the number 0 and R5 is hydrogen or 1-4C-alkyl.

1-4C-Alkyl represents straight-chain or branched alkyl radicals having 1 to 4 carbon atoms. Examples which may be mentioned are the butyl, isobutyl, sec-butyl, tert-butyl, propyl, isopropyl, ethyl and methyl radical.

1-4C-Alkoxy is a radical which besides the oxygen atom contains one of the abovementioned 1-4C-alkyl radicals. Examples which may be mentioned are the methoxy and ethoxy radical.

Halogen within the meaning of the present invention is bromine, chlorine and fluorine.

Completely or predominantly fluorine-substituted 1-4C-alkoxy which may be mentioned, for example, are the 1,2,2-trifluoroethoxy, the 2,2,3,3,3-pentafluoropropoxy, the perfluoroethoxy and in particular the 1,1,2,2-tetrafluoroethoxy, the trifluoromethoxy, the 2,2,2-trifluoroethoxy and the difluoromethoxy radical.

If desired completely or partially fluorine-substituted 1-2C-alkylenedioxy which may be mentioned, for example, are the methylenedioxy (—O—$CH_2$—O—), the ethylenedioxy (—O—$CH_2$—$CH_2$—O—), the 1,1-difluoroethylene -dioxy (—O—CF$_2$—CH$_2$—O—), the 1,1,2,2-tetrafluoroethylenedioxy (—O—CF$_2$—CF$_2$—O—) and in particular the difluoromethylenedioxy (—O—CF$_2$—O—) and the 1,1,2-trifluoroethylenedioxy radical (—O—CF$_2$—CHF—O—).

If R2 and R3 together, if desired, are completely or partially fluorine-substituted 1-2C-alkylenedioxy or chlorotrifluoroethylenedioxy, the substituents R2 and R3 are bonded in neighboring positions—preferably to positions 5 and 6—on the benzo moiety of the benzimidazole ring.

Exemplary, R14-substituted 1-4C-alkyl radicals which may be mentioned are the 2-methoxycarbonylethyl, the 2-ethoxycarbonylethyl, the methoxycarbonylmethyl, the carboxymethyl, the 2-hydroxyethyl, the methoxymethyl, the 2-methoxyethyl, the dimethylaminomethyl and the 2-dimethylaminoethyl radical.

1-4C-Alkylcarbonyl is a radical which besides the carbonyl group contains one of the abovementioned 1-4C-alkyl radicals. An example which may be mentioned is the acetyl radical.

2-4C-Alkenylcarbonyl is a radical which besides the carbonyl group contains a 2-4C-alkenyl radical, for example a propenyl radical or a butenyl radical. An example which may be mentioned is the acryloyl radical.

Halo-1-4C-alkylcarbonyl is a radical which besides the carbonyl group contains a halo-substituted 1-4C-alkyl radical. An example which may be mentioned is the γ-chlorobutyryl radical.

N(R15)R16-1-4C-Alkylcarbonyl is a radical which besides the carbonyl group contains an —N(R15)R16-substituted 1-4C-alkyl radical. An example which may be mentioned is the 3-dimethylaminopropionyl radical.

Di-1-4C-alkylcarbamoyl is a radical which besides the carbonyl group contains a di-1-4C-alkylamino radical. The di-1-4C-alkylamino radical is an amino radical which is substituted by two 1-4C-alkyl radicals which are identical to or different from the abovementioned 1-4C-alkyl radicals. Examples which may be mentioned are the dimethylamino, the diethylamino and the diisopropylamino radical. Di-1-4C-alkylcarbamoyl radicals which may be mentioned are, for example, the dimethylcarbamoyl and the diethylcarbamoyl radical.

1-4C-Alkylsulfonyl is a radical which besides the sulfonyl group (—SO$_2$—) contains one of the abovementioned 1-4C-alkyl radicals. An example which may be mentioned is the methylsulfonyl radical.

Mono- or di-1-4C-alkylcarbamoyl radicals are carbamoyl radicals (—CO—NH$_2$) which are substituted by one or two 1-4C-alkyl radicals which are identical to or different from the abovementioned 1-4C-alkyl radicals. Examples which may be mentioned are the methylcarbamoyl, the isopropylcarbamoyl and the dimethylcarbamoyl radical.

Mono- or di-1-4C-alkylthiocarbamoyl radicals are thincarbamoyl radicals (—CS—NH$_2$), which are substituted by one or two 1-4C-alkyl radicals which are identical to or different from the abovementioned 1-4C-alkyl radicals. Examples which may be mentioned are the methylthiocarbamoyl, the isopropylthiocarbamoyl and the dimethylthiocarbamoyl radical.

An N-1-4C-alkyl-N'-cyanoamidino radical which may be mentioned as an example is in particular the N-methyl-N'-cyanoamidino radical [—C(=NCN)—NH—CH$_3$].

A 1-N-1-4C-alkylamino-2-nitroethylene radical which may be mentioned as an example is in particular the 1-N-methylamino-2-nitroethylene radical [—C(NHCH$_3$)=CHNO$_2$].

Exemplary radicals —Y—C$_u$H$_{2u}$—R6 where R6=an N-1-4C-alkyl-N'-cyanoamidino radical, 1-N-1-4C-alkyl-amino-2-nitroethylene radical or N-2-propynyl-N'-cyano-amidino radical are in particular those radicals in which Y has the meaning NH and u is the number 0. In this connection, as the radical —Y—C$_u$H$_{2u}$—R6 particular mention may be made of the radicals —NH—C(=NCN)NH—CH$_3$, —NH—C(NHCH$_3$)=CHNO$_2$ and —NH—C(=NCN)NH—CH$_2$C≡CH.

The group C$_u$H$_{2u}$ is preferably bound to a carbon atom of the cyclic system or bicyclic system R6 concerned, so that radicals R6 (if R6 is a cyclic system or bicyclic system) which may be mentioned as examples are the radicals: phenyl, 2-furyl, 3-furyl, 2-thienyl, 3-thienyl, 3-pyrrolyl, 2-oxazolyl, 4-oxazolyl, 4-isoxazolyl, 5-isoxazolyl, 2-thiazolyl, 3-isothiazolyl, 2-imidazolyl, 3-pyra-zolyl, 4-pyrazolyl, 1,2,3-triazol-4-yl, 1,2,5-thiadiazol-4-yl, 1,2,5-thiadiazol-4-yl-1-oxide, 1,2,4-triazol-3-yl, tetrazol-5-yl, 1,3,4-thiadiazol-2-yl, 1,2,3-thiadiazol-4-yl, 1,2,5-thiadiazol-4-yl, 1,2,5-thiadiazol-4-yl-1-oxide, 1,3,4-oxadiazol-2-yl, 2-pyridyl, 4-pyridyl, 2-pyrimidinyl, 1,3,4-triazin-2-yl, 2-benzimidazolyl, 2-imidazopyridyl, 2-benzothiazolyl and 2-benzoxazolyl.

1-4C-Alkoxycarbonyl is a radical which besides the carbonyl group contains one of the abovementioned 1-4C-alkoxy radicals. Examples which may be mentioned are the methoxycarbonyl and the ethoxycarbonyl radical.

The substitutents R8 and R9 can be bonded into the cyclic systems or bicyclic systems R6 at any conceivable position. Exemplary, R8- and R9-substituted radicals R6 which may be mentioned are: 4-methylphenyl, 3-dimethylaminomethylphenyl, 3-piperidinomethylphenyl, 3-carboxymethylphenyl, 2-dimethylaminomethyl-5-methyl-3-furyl, 1-methylpyrrol-3-yl, 4,5-dimethyloxazol-2-yl, 3,5-dimethylisoxazol-4-yl, 4,5-dimethylthiazol-2-yl, 4-methyl-5-carboxymethylthiazol-2-yl, 1-methylimidazol-2-yl, 1-methylpyrazol-3-yl, 1-(2-dimethylaminoethyl)-pyrazol-3-yl, 5-methyl-1,3,4-oxadiazol-2-yl, 1-methyl-1,2,3-triazol-4-yl, 1-methyl-1,2,4-triazol-3-yl, 1-(2-dimethylaminoethyl)-1,2,3-triazol-4-yl, 1-methyltetrazol-5-yl, 1-(2-dimethylaminoethyl) tetrazol-5-yl, 1-carboxymethyltetrazol-5-yl, 5-methyl-1,3,4-thiadiazol-2-yl, 5-trifluoromethyl-1,3,4-thiadiazol-2-yl, 1-(2-hydroxyethyl) tetrazol-5-yl, 2-amino-1,3,4-thiadiazol-2-yl, 3-amino-1,2,4-triazol-5-yl, 4-methyl-5-trifluoromethyl-1,2,4-triazol-3-yl and 4-aminopyrimidin-2-yl.

Possible radicals —C$_m$H$_{2m}$—, —CrH$_{2r}$— and 'C$_u$H$_{2u}$— are straight-chain or branched radicals. Examples which may be mentioned are the heptylene, isoheptylene (2-methylhexylene), hexylene, isohexylene (2-methylpentylene), neohexylene (2,2-dimethylbutylene), pentylene, isopentylene (3-methylbutylene), neopentylene (2,2-dimethylpropylene), butylene, isobutylene, sec-butylene, tertbutylene, propylene, isopropylene, ethylene and (for —C$_u$H$_{2u}$) the methylene radical.

Radicals —C$_m$H$_{2m}$ which may preferably be mentioned are the ethylene (—CH$_2$CH$_2$—) and the butylene (—CH$_2$CH$_2$CH$_2$CH$_2$—) and in particular the propylene radical (—CH$_2$CH$_2$CH$_2$—).

Radicals —C$_r$H$_{2r}$— which may preferably be mentioned are the ethylene, the propylene and the butylene radical.

Radicals —C$_u$H$_{2u}$— which may preferably be mentioned are the methylene, the ethylene and the propylene radical. In a further preferred embodiment, u is the number 0, so that the term C$_u$H$_{2u}$ disappears or is a bonding dash and the radical R6 is directly bonded to the group Y.

In a further preferred embodiment, t is the number 0, so that the term S(=O)$_q$—CrH$_{2r}$ disappears or is a bonding dash and the group Y is bonded directly to the group C$_m$H$_{2m}$.

Exemplary radicals bonded in the 4-position on the pyridine ring to the group S(=O)p which may be mentioned are: phenylthiopentyl, phenylthioethyl, phenylthiopropyl, phenylthiobutyl, 4-methylphenylthioethyl, 4-methylphenylthiopropyl, 3-dimethylaminomethylphenylthioethyl, 3-dimethylaminomethylphenylthiopropyl, 3-piperidinomethylphenylthioethyl, 3-piperidinomethylphenylthiopropyl, 3-piperidinomethylphenylthiobutyl, 1-methylpyrrol-3-thioethyl, 4,5-dimethyloxazole-2-thiopropyl, 3,5-dimethylisoxazole-5-thioethyl, 3,5-dimethylisoxazole-5-thiopropyl, thiazole-2-thioethyl, thiazole-2-thiopropyl thiazole-2-thiobutyl, 4-methyl-5-carboxymethylthiazole-2-thiopropyl, 1-methylimidazole-2-thioethyl, 1-methylimidazole-2-thiopropyl, 1-methylimidazole-2-thiobutyl, imidazole-2-thioethyl, imidazole-2-thiopropyl, pyrazole-3-thiopropyl, 1-(2-dimethylaminoethyl) pyrazole-2-thioethyl, 1,3,4-oxadiazole-2-thioethyl, 1,3,4-oxadiazole-2-thiopropyl, 1,2,3-triazole-4-thioethyl, 1,2,3-triazole-4-thiopropyl, 1,2,3-triazole-4-thiobutyl, 1-methyl-1,2,3-triazole-4-thioethyl, 1-methyl-1,2,3-triazole-4-thiopropyl, 1,2,4-triazole-3-thioethyl, 1,2,4-triazole-3-thiopropyl, 3-amino-1,2,4-triazole-5-thioethyl, 3-amino-1,2,4-triazole-5-thiopropyl, 4-methyl-5-trifluoromethyl-1,2,4-triazole-3-thioethyl, 4-methyl-5-trifluoromethyl-1,2,4-triazole-3-thiopropyl, 1-methyl-1,2,4-triazole-3-thioethyl, 1-methyl-1, 2,4-triazole-3-thiopropyl, 1-methyl-1,2,4-triazole-3-thiobutyl, tetrazole-5-thioethyl, tetrazole-5-thiopropyl, tetrazole-5-thiobutyl, 1-methyltetrazole-5-thioethyl, 1-methyltetrazole-5-thiopropyl, 1-methyltetrazole-5-thiobutyl, 1-(2-dimethylaminoethyl) tetrazole-5-thioethyl, 1-(2-dimethylaminoethyl) tetrazole-5-thiopropyl, 1-(2-hydroxyethyl) tetrazole-5-thioethyl, 1-(2-hydroxyethyl) tetrazole-5-thiopropyl, 1,3,4-thiadiazole-2-thioethyl, 1,3,4-thiadiazole-2-thiopropyl, 5-methyl-1,3,4-thiadiazole-2-thioethyl, 5-methyl-1,3,4-thiadiazole-2-thiopropyl, 5-methyl-1,3,4-thiadiazole-2-thiobutyl, 5-trifluoromethyl-1, 3,4-thiadiazole-2-thioethyl, 5-trifluoromethyl-1,3,4-thiadiazole-2-thiopropyl, 1,2,3-thiadiazole-4-thioethyl, 1,2, 3-thiadiazole-4-thiopropyl, 1-carboxymethyltetrazole-5-thioethyl, 1-carboxymethyltetrazole-5-thiopropyl, 2-pyridylthioethyl, 2-pyridylthiopropyl, 2-pyridylthiobutyl, 4-pyridylthioethyl, 4-pyridylthiopropyl, 4-pyridylthiobutyl, 2-pyrimidinethioethyl, 2-pyrimidinethiopropyl, 2-pyrimidinethiobutyl, 4-aminopyrimidine-2-thioethyl, 4-aminopyrimidine-2-thiopropyl, 2-benzimidazolethioethyl, 2-benzimidazolethiopropyl, 4-methylthiazole-5-ethylthiopropyl, 2-guanidinothiazole-4-methylthiopropyl, furyl-2-methylthiopropyl, 5-dimethylaminomethylfuryl-2-methylthiopropyl, imidazopyridine-2-thiopropyl, benzoxazole-2-thiopropyl, benzothiazole-2-thiopropyl, 4-methylphenylmethylthiopropyl, dimethylcarbamoylthiopropyl, dimethylthiocarbamoylthiopropyl, N-methyl-N'-cyanoamidinothiopropyl, phenoxyethyl, phenoxypropyl, 4-methylthiazole-5-ethylthioethyl, 2-guanidinothiazole-4-methylthioethyl, furyl-2-methylthioethyl, 5-dimethylaminomethylfuryl-2-methylthioethyl, imidazopyridin-2-thioethyl, benzoxazole-2-thioethyl, benzothiazole-2-thioethyl, 4-methylphenylmethylthioethyl, dimethylcarbamoylthioethyl, dimethylthiocarbamoylthioethyl, N-methyl-N'-cyanoamidinothioethyl, 4-methylthiazole-5-ethylthiobutyl, 2-guanidinothiazole-4-methylthiobutyl, furyl-2-methylthiobutyl, 5-dimethylaminomethylfuryl-2-methylthiobutyl, imidazopyridine-2-thiobutyl, benzoxazole-2-thiobutyl, benzothiazole-2-thiobutyl, 4-methylphenylmethylthiobutyl, dimethylcarbamoylthiobutyl, dimethylthiocarbamoylthiobutyl, N-methyl-N'-cyanoamidinothiobutyl, 4-methylthiazole-5-thioethyl, 4-methyithiazole-5-thiopropyl, 4-methylthiazole-5-thiobutyl, 1-methoxycarbonylmethyltetrazole-5-thioethyl, 1-methoxycarbonylmethyltetrazole-5-propyl, 1-methoxycarbonylmethyltetrazole-5-butyl, thienyl-2-methylthioethyl, thienyl-2-methylthiopropyl, thienyl-2-methylthiobutyl, thienyl-2-ethylthioethyl, thienyl-2-ethylthiopropyl, thienyl-2-ethylthiobutyl, 5-chlorothienyl-2-methylthioethyl, 5-chlorothienyl-2-methylthiopropyl, 5-chlorothienyl-2-methylthiobutyl, 4-pyridylmethylthioethyl, 4-pyridylmethylthiopropyl, 4-pyridylmethylthiobutyl, 2-pyridylmethylthioethyl, 2-pyridylmethylthiopropyl, 2-pyridylmethylthiobutyl, 2-pyridinylethylthioethyl, 2-pyridinylethylthiopropyl, 2-pyridinylethylthiobutyl, 3-dimethylaminomethylphenylmethylthioethyl, 3-dimethylaminomethylphenylmethylthiopropyl, 3-dimethylaminomethylphenylmethylthiobutyl, 2-benzimidazolemethylthiopropyl, 2-benzimidazolemethylthiobutyl, 5-nitroimidazole-1-ethylthioethyl, 5-nitroimidazole-1-ethylthiopropyl, 5-nitroimidazole-1-ethylthiobutyl, 2-methyl-5-nitroimidazole-1-ethylthioethyl, 2-methyl-5-nitroimidazole-1-ethylthiopropyl, 2-methyl-5-nitroimidazole-1-ethylthiobutyl, 5-nitroimidazole-1-propylthioethyl, 5-nitroimidazole-1-propylthiopropyl, 5-nitroimidazole-1-propylthiobutyl, 2-methyl-5-nitroimidazole-1-propylthioethyl, 2-methyl-5-nitroimidazole-1-propylthiopropyl, 2-methyl-5-nitroimidazoie-1-propylthiobutyl.

Suitable salts of compounds of the formula I in which n is the number 0 are all acid addition salts. The pharmacologically tolerable salts of the inorganic and organic acids customarily used in pharmacy may be particularly mentioned. Pharmacologically non-tolerable salts, which can initially be obtained, for example, as process products in the preparation of the compounds according to the invention on the industrial scale, are converted into pharmacologically tolerable salts by methods known to the person skilled in the art. Those suitable are water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)-benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, the acids being employed in salt preparation—depending on whether a mono- or polybasic acid is concerned and depending on which salt is desired—in an equimolar quantitative ratio or one differing therefrom.

For compounds of the formula I in which n is the number 1 and/or for compounds having a carboxyl radical, suitable salts are also salts with bases. Examples of basic salts which may be mentioned are lithium, sodium, potassium, calcium, aluminum, magnesium, titanium, ammonium, meglumine or guanidinium salts, the bases being also employed here in salt preparation in an equimolar quantitative ratio or one differing therefrom.

One embodiment of the invention are compounds of the formula I in which X has the meaning CH.

A further embodiment of the invention are compounds of the formula I in which X has the meaning N.

A further embodiment of the invention are compounds of the formula I in which t is tile number 1.

A further embodiment of the invention are compounds of the formula I in which u is a number from 1 to 7.

A further embodiment of the invention are compounds of the formula I in which Y has the meaning O (oxygen).

A further embodiment of the invention are compounds of the formula I in which X has the meaning CH, Y has the meaning S, t is the number 0 and u is a number from 1 to 7.

A further embodiment of the invention are compounds of the formula I in which X has the meaning CH, Y has the meaning S, t is the number 0, u is the number 0 and R4 is R14-substituted 1-4C-alkyl, 1-4C-alkylcarbonyl, 2-4C-alkenylcarbonyl, halo-1-4C-alkylcarbonyl, N(R15)R16-1-4C-alkylcarbonyl, di-1-4C-alkylcarbamoyl or 1-4C-alkylsulfonyl.

A further embodiment of the invention are compounds of the formula I in which Y has the meaning S, t is the number 0, u is the number 0 and R6 is a mono- or di-1-4C-alkylcarbamoyl or thiocarbamoyl radical, an N-1-4C-alkyl-N'-cyanoamidino radical, a 1-N-1-4C-alkylamino-2-nitroethylene radical, an N-2-propynyl-N'-cyanoamidino radical, an aminosulfonylamidino radical, or an R8- and R9-substituted cyclic system which is selected from the group consisting of thiadiazole-1-oxide, triazine, pyridone, imidazopyridine, benzothiazole and benzoxazole.

A further embodiment of the invention are compounds of the formula I in which Y is NH or N-1-4C-alkyl, t is the number 0 and R5 is 1-4C-alkoxy.

Compounds of the formula I to be emphasized are those in which

X is CH or N,

Y is S, SO$_2$, O or N-1-4C-alkyl,

R1 is hydrogen, 1-4C-alkoxy or halogen,

R2 is hydrogen, 1-4C-alkyl, 1-4C-alkoxy or halogen,

R3 is hydrogen,

R4 is hydrogen, R14-substituted 1-4C-alkyl, N(R15)R16-1-4C-alkylcarbonyl or 1-4C-alkylsulfonyl, R5 is hydrogen, 1-4C-alkyl or 1-4C-alkoxy, R6 is a mono- or di-1-4C-alkylthiocarbamoyl radical, an N-1-4C-alkyl-N'-cyanoamidino radical, a 1-N-1-4C-alkylamino-2-nitroethylene radical, an N-2-propynyl-N'-cyanoamidino radical, or an R8- and R9-substituted cyclic system or bicyclic system which is selected from the group consisting of benzene, furan, thiophene, oxazole, isoxazole, thiazole, thiazoline, isothiazole, imidazole, pyrazole, triazole, tetrazole, thiadiazole, thiadiazole-1-oxide, oxadiazole, pyridine, pyrimidine, triazine, pyridone, benzimidazole, imidazopyridine, benzothiazole and benzoxazole, R7 is hydrogen or 1-4C-alkyl, R8 is hydrogen, 1-4C-alkyl, hydroxyl, nitro, guanidino, carboxyl, 1-4C-alkoxycarbonyl or R10-substituted 1-4C-alkyl, R9 is hydrogen, 1-4C-alkyl, hydroxyl, 1-4C-alkoxy or fluorine, R10 is hydroxyl, 1-4C-alkoxy, carboxyl, 1-4C-alkoxycarbonyl or —N(R11)R12, where R11 is 1-4C-alkyl or —CO—R13 and R12 is 1-4C-alkyl, or where R11 and R12, together and including the nitrogen atom to which both are bonded, are a piperidino or morpholino radical, R13 is 1-4C-alkyl, R14 is hydroxyl, 1-4C-alkoxycarbonyl or —N(R15)R16, where R15 is 1-4C-alkyl and R16 is 1-4C-alkyl, or where R15 and R16, together and including the nitrogen atom to which both are bonded, are a piperidino or morpholino radical, m is a number from 2 to 4, n is the number 0 or 1, p is the number 0, q is the number 0 or 2, r is a number from 2 to 4, t is the number 0 or 1 and u is a number from 0 to 3 and their salts, those compounds of the formula I being excluded in which Y is S and, at the same time, X is CH, t is the number 0, u is the number 0, R4 is hydrogen and R6 is an R8- and R9-substituted cyclic system or bicyclic system which is selected from the group consisting of benzene, furan, thiophene, oxazole, isoxazole, thiazole, thiazoline, isothiazole, imidazole, pyrazole, triazole, tetrazole, thiadiazole, oxadiazole, pyridine, pyrimidine and benzimidazole, and where furthermore those compounds of the formula I are excluded in which Y is N-1-4C-alkyl and, at the same time, t is the number 0 and R5 is hydrogen or 1-4C-alkyl.

Compounds of the formula I particularly to be emphasized are those in which

X is CH or N,

Y is S or SO$_2$,

R1 is hydrogen, 1-4C-alkoxy or fluorine,

R2 is hydrogen, 1-4C-alkyl or fluorine,

R3 is hydrogen,

R4 is hydrogen, R14-substituted 1-4C-alkyl or 1-4C-alkylsulfonyl,

R5 is hydrogen or 1-4C-alkyl,

R6 is a di-1-4C-alkylthiocarbamoyl radical, an N-1-4C-alkyl-N'-cyanoamidino radical or an RB- and R9-substituted cyclic system which is selected from the group consisting of benzene, furan, thiophene, thiazole, imidazole, triazole, tetrazole, thiadiazole, pyridine, pyrimidine and triazine, R7 is hydrogen or 1-4C-alkyl, R8 is hydrogen, 1-4C-alkyl, hydroxyl, nitro, guanidino, carboxyl, 1-4C-alkoxycarbonyl or R10-substituted 1-4C-alkyl, R9 is hydrogen, 1-4C-alkyl, hydroxyl or fluorine, R10 is hydroxyl, 1-4C-alkoxycarbonyl or —N(R11)R12, where R11 is 1-4C-alkyl and R12 is 1-4C-alkyl, or where R11 and R12, together and including the nitrogen atom to which both are bonded, are a piperidino or morpholino radical, R14 is 1-4C-alkoxycarbonyl or —N(R15)R16, where R15 is 1-4C-alkyl and R16 is 1-4C-alkyl, or where R15 and R16, together and including the nitrogen atom to which both are bonded, are a piperidino or morpholino radical, m is a number from 2 to 4, n is the number 0, p is the number 0, t is the number 0 and u is a number from 0 to 3 and their salts, those compounds of the formula I being excluded in which Y is S and, at the same time, X is CH, u is the number 0, R4 is hydrogen and R6 is an R8- and R9-substituted cyclic system which is selected from the group consisting of benzene, furan, thiophene, thiazole, imidazole, triazole, tetrazole, thiadiazole, pyridine and pyrimidine.

Preferred compounds of the formula I are those in which x is CH or N,

Y is S or $SO_2$,

R1 is hydrogen, 1-4C-alkoxy or fluorine,

R2 is hydrogen or fluorine,

R3 is hydrogen,

R4 is hydrogen,

R5 is 1-4C-alkyl,

R6 is a di-1-4C-alkylthiocarbamoyl radical or an R8- and R9-substituted cyclic system which is selected from the group consisting of benzene, furan, thiophene, thiazoLe, imidazole, triazole, tetrazole, thiadiazole, pyridine and pyrimidine, R7 is hydrogen, R8 is hydrogen, nitro, 1-4C-alkoxycarbonyl or R10-substituted 1-2C-alkyl, R9 is hydrogen or 1-4C-alkyl, R10 is 1-4C-alkoxycarbonyl or —N(R11)R12, where R11 is 1-4C-alkyl and R12 is 1-4C-alkyl, or where R11 and R12, together and including the nitrogen atom to which both are bonded, are a piperidino or morpholino radical, m is the number 2 or 3, n is the number 0, p is the number 0, t is the number 0 and u is a number from 1 to 3 and their salts.

One embodiment of the preferred compounds are those in which X has the meaning CH.

A further embodiment of the preferred compounds are those in which X has the meaning N.

A further embodiment of the preferred compounds are those in which Y has the meaning S.

A further embodiment of the preferred compounds are those in which R1 and R2 are hydrogen.

A further embodiment of the prefered compounds are those in which u is the number 1.

A further embodiment of the prefered compounds are those in which u is the number 2.

A further embodiment of the preferred compounds are those in which m is the number 2.

A further embodiment of the preferred compounds are those in which m is the number 3.

Particularly preferred compounds of the formula I are those in which

X is CH or N,

Y is S,

R1 is hydrogen,

R2 is hydrogen,

R3 is hydrogen,

R4 is hydrogen,

R5 is 1-4C-alkyl,

R6 is an R8- and R9-substituted cyclic system which is selected from the group consisting of benzene, furan, thiophene, thiazole, imidazole, triazole, tetrazole, thiadiazole, pyridine and pyrimidine, R7 is hydrogen, R8 is nitro, R9 is hydrogen or 1-4C-alkyl, m is the number 2 or 3, n is the number 0, p is the number 0, t is the number 0 and u is a number from 1 to 3 and their salts.

Very particularly preferred compounds of the formula I are those in which

X is CH or N,

Y is S,

R1 is hydrogen,

R2 is hydrogen,

R3 is hydrogen,

R4 is hydrogen,

R5 is 1-4C-alkyl,

R6 is R8- and R9-substituted imidazole,

R7 is hydrogen,

R8 is nitro,

R9 is hydrogen or 1-4C-alkyl, m is the number 2 or 3, n is the number 0, p is the number 0, t is the number 0 and u is a number from 1 to 3 and their salts.

Exemplary compounds according to the invention are listed in the following tables:

TABLE 1

Compounds of the formula I (see attached formula sheet I) where n = 0, p = 0, q = 0, R6 = dimethyl-carbamoyl and with the following further substituent meanings:

| X  | Y   | R1   | R2 | R3 | R4 | R5  | R7 | m | r | t | u |
|----|-----|------|----|----|----|-----|----|----|---|---|---|
| CH | S   | H    | H  | H  | H  | $CH_3$ | H | 2 | — | 0 | 0 |
| CH | S   | $OCH_3$ | H  | H  | H  | $CH_3$ | H | 2 | — | 0 | 0 |
| CH | S   | F    | H  | H  | H  | $CH_3$ | H | 2 | — | 0 | 0 |
| CH | S   | F    | F  | H  | H  | $CH_3$ | H | 2 | — | 0 | 0 |
| CH | S   | H    | H  | H  | H  | $CH_3$ | H | 3 | — | 0 | 0 |
| CH | S   | $OCH_3$ | H  | H  | H  | $CH_3$ | H | 3 | — | 0 | 0 |
| CH | S   | F    | H  | H  | H  | $CH_3$ | H | 3 | — | 0 | 0 |
| CH | S   | F    | F  | H  | H  | $CH_3$ | H | 3 | — | 0 | 0 |
| N  | S   | H    | H  | H  | H  | $CH_3$ | H | 2 | — | 0 | 0 |
| N  | S   | $OCH_3$ | H  | H  | H  | $CH_3$ | H | 2 | — | 0 | 0 |
| N  | S   | F    | H  | H  | H  | $CH_3$ | H | 2 | — | 0 | 0 |
| N  | S   | F    | F  | H  | H  | $CH_3$ | H | 2 | — | 0 | 0 |
| N  | S   | H    | H  | H  | H  | $CH_3$ | H | 3 | — | 0 | 0 |
| N  | S   | $OCH_3$ | H  | H  | H  | $CH_3$ | H | 3 | — | 0 | 0 |
| N  | S   | F    | H  | H  | H  | $CH_3$ | H | 3 | — | 0 | 0 |
| N  | S   | F    | F  | H  | H  | $CH_3$ | H | 3 | — | 0 | 0 |
| CH | $SO_2$ | H    | H  | H  | H  | $CH_3$ | H | 2 | — | 0 | 0 |
| CH | $SO_2$ | $OCH_3$ | H  | H  | H  | $CH_3$ | H | 2 | — | 0 | 0 |
| CH | $SO_2$ | F    | H  | H  | H  | $CH_3$ | H | 2 | — | 0 | 0 |
| CH | $SO_2$ | F    | F  | H  | H  | $CH_3$ | H | 2 | — | 0 | 0 |
| CH | $SO_2$ | H    | H  | H  | H  | $CH_3$ | H | 3 | — | 0 | 0 |
| CH | $SO_2$ | $OCH_3$ | H  | H  | H  | $CH_3$ | H | 3 | — | 0 | 0 |
| CH | $SO_2$ | F    | H  | H  | H  | $CH_3$ | H | 3 | — | 0 | 0 |
| CH | $SO_2$ | F    | F  | H  | H  | $CH_3$ | H | 3 | — | 0 | 0 |
| N  | $SO_2$ | H    | H  | H  | H  | $CH_3$ | H | 2 | — | 0 | 0 |
| N  | $SO_2$ | $OCH_3$ | H  | H  | H  | $CH_3$ | H | 2 | — | 0 | 0 |
| N  | $SO_2$ | F    | H  | H  | H  | $CH_3$ | H | 2 | — | 0 | 0 |

TABLE 1-continued

Compounds of the formula I (see attached formula sheet I) where n = 0, p = 0, q = 0, R6 = dimethyl-carbamoyl and with the following further substituent meanings:

| X | Y | R1 | R2 | R3 | R4 | R5 | R7 | m | r | t | u |
|---|---|---|---|---|---|---|---|---|---|---|---|
| N | SO$_2$ | F | F | H | H | CH$_3$ | H | 2 | — | 0 | 0 |
| N | SO$_2$ | H | H | H | H | CH$_3$ | H | 3 | — | 0 | 0 |
| N | SO$_2$ | OCH$_3$ | H | H | H | CH$_3$ | H | 3 | — | 0 | 0 |
| N | SO$_2$ | F | H | H | H | CH$_3$ | H | 3 | — | 0 | 0 |
| N | SO$_2$ | F | F | H | H | CH$_3$ | H | 3 | — | 0 | 0 |

TABLE 2

Compounds of the formula I (see attached formula sheet I) where n = 0, p = 0, q = 0, R6 = dimethylthio-carbamoyl and with the following further substituent meanings:

| X | Y | R1 | R2 | R3 | R4 | R5 | R7 | m | r | t | u |
|---|---|---|---|---|---|---|---|---|---|---|---|
| CH | S | H | H | H | H | CH$_3$ | H | 2 | — | 0 | 0 |
| CH | S | OCH$_3$ | H | H | H | CH$_3$ | H | 2 | — | 0 | 0 |
| CH | S | F | H | H | H | CH$_3$ | H | 2 | — | 0 | 0 |
| CH | S | F | F | H | H | CH$_3$ | H | 2 | — | 0 | 0 |
| CH | S | H | H | H | H | CH$_3$ | H | 3 | — | 0 | 0 |
| CH | S | OCH$_3$ | H | H | H | CH$_3$ | H | 3 | — | 0 | 0 |
| CH | S | F | H | H | H | CH$_3$ | H | 3 | — | 0 | 0 |
| CH | S | F | F | H | H | CH$_3$ | H | 3 | — | 0 | 0 |
| N | S | H | H | H | H | CH$_3$ | H | 2 | — | 0 | 0 |
| N | S | OCH$_3$ | H | H | H | CH$_3$ | H | 2 | — | 0 | 0 |
| N | S | F | H | H | H | CH$_3$ | H | 2 | — | 0 | 0 |
| N | S | F | F | H | H | CH$_3$ | H | 2 | — | 0 | 0 |
| N | S | H | H | H | H | CH$_3$ | H | 3 | — | 0 | 0 |
| N | S | OCH$_3$ | H | H | H | CH$_3$ | H | 3 | — | 0 | 0 |
| N | S | F | H | H | H | CH$_3$ | H | 3 | — | 0 | 0 |
| N | S | F | F | H | H | CH$_3$ | H | 3 | — | 0 | 0 |
| CH | SO$_2$ | H | H | H | H | CH$_3$ | H | 2 | — | 0 | 0 |
| CH | SO$_2$ | OCH$_3$ | H | H | H | CH$_3$ | H | 2 | — | 0 | 0 |
| CH | SO$_2$ | F | H | H | H | CH$_3$ | H | 2 | — | 0 | 0 |
| CH | SO$_2$ | F | F | H | H | CH$_3$ | H | 2 | — | 0 | 0 |
| CH | SO$_2$ | H | H | H | H | CH$_3$ | H | 3 | — | 0 | 0 |
| CH | SO$_2$ | OCH$_3$ | H | H | H | CH$_3$ | H | 3 | — | 0 | 0 |
| CH | SO$_2$ | F | H | H | H | CH$_3$ | H | 3 | — | 0 | 0 |
| CH | SO$_2$ | F | F | H | H | CH$_3$ | H | 3 | — | 0 | 0 |
| N | SO$_2$ | H | H | H | H | CH$_3$ | H | 2 | — | 0 | 0 |
| N | SO$_2$ | OCH$_3$ | H | H | H | CH$_3$ | H | 2 | — | 0 | 0 |
| N | SO$_2$ | F | H | H | H | CH$_3$ | H | 2 | — | 0 | 0 |
| N | SO$_2$ | F | F | H | H | CH$_3$ | H | 2 | — | 0 | 0 |
| N | SO$_2$ | H | H | H | H | CH$_3$ | H | 3 | — | 0 | 0 |
| N | SO$_2$ | OCH$_3$ | H | H | H | CH$_3$ | H | 3 | — | 0 | 0 |
| N | SO$_2$ | F | H | H | H | CH$_3$ | H | 3 | — | 0 | 0 |
| N | SO$_2$ | F | F | H | H | CH$_3$ | H | 3 | — | 0 | 0 |

TABLE 3

Compounds of the formula I (see attached formula sheet I) where n = 0, p = 0, q = 0, R6 = N-methyl-N'-cyanoamidino and with the following further substituent meanings:

| X | Y | R1 | R2 | R3 | R4 | R5 | R7 | m | r | t | u |
|---|---|---|---|---|---|---|---|---|---|---|---|
| CH | S | H | H | H | H | CH$_3$ | H | 2 | — | 0 | 0 |
| CH | S | F | H | H | H | CH$_3$ | H | 2 | — | 0 | 0 |
| CH | S | H | H | H | H | CH$_3$ | H | 3 | — | 0 | 0 |
| CH | S | F | H | H | H | CH$_3$ | H | 3 | — | 0 | 0 |
| CH | NH | H | H | H | H | OCH$_3$ | H | 2 | — | 0 | 0 |
| CH | NH | F | H | H | H | OCH$_3$ | H | 2 | — | 0 | 0 |
| CH | NH | H | H | H | H | OCH$_3$ | H | 3 | — | 0 | 0 |
| CH | NH | F | H | H | H | OCH$_3$ | H | 3 | — | 0 | 0 |
| N | S | H | H | H | H | CH$_3$ | H | 2 | — | 0 | 0 |
| N | S | F | H | H | H | CH$_3$ | H | 2 | — | 0 | 0 |
| N | S | H | H | H | H | CH$_3$ | H | 3 | — | 0 | 0 |
| N | S | F | H | H | H | CH$_3$ | H | 3 | — | 0 | 0 |
| N | NH | H | H | H | H | OCH$_3$ | H | 2 | — | 0 | 0 |
| N | NH | F | H | H | H | OCH$_3$ | H | 2 | — | 0 | 0 |
| N | NH | H | H | H | H | OCH$_3$ | H | 3 | — | 0 | 0 |
| N | NH | F | H | H | H | OCH$_3$ | H | 3 | — | 0 | 0 |

TABLE 4

Compounds of the formula I (see attached formula sheet I) where n = 0, p = 0, q = 0, R6 = 1-N-methyl-2-nitroethyl and with the following further substituent meanings:

| X | Y | R1 | R2 | R3 | R4 | R5 | R7 | m | r | t | u |
|---|---|---|---|---|---|---|---|---|---|---|---|
| CH | S | H | H | H | H | CH$_3$ | H | 2 | — | 0 | 0 |
| CH | S | F | H | H | H | CH$_3$ | H | 2 | — | 0 | 0 |
| CH | S | H | H | H | H | CH$_3$ | H | 3 | — | 0 | 0 |
| CH | S | F | H | H | H | CH$_3$ | H | 3 | — | 0 | 0 |
| CH | NH | H | H | H | H | OCH$_3$ | H | 2 | — | 0 | 0 |
| CH | NH | F | H | H | H | OCH$_3$ | H | 2 | — | 0 | 0 |
| CH | NH | H | H | H | H | OCH$_3$ | H | 3 | — | 0 | 0 |
| CH | NH | F | H | H | H | OCH$_3$ | H | 3 | — | 0 | 0 |
| N | S | H | H | H | H | CH$_3$ | H | 2 | — | 0 | 0 |
| N | S | F | H | H | H | CH$_3$ | H | 2 | — | 0 | 0 |
| N | S | H | H | H | H | CH$_3$ | H | 3 | — | 0 | 0 |
| N | S | F | H | H | H | CH$_3$ | H | 3 | — | 0 | 0 |
| N | NH | H | H | H | H | OCH$_3$ | H | 2 | — | 0 | 0 |
| N | NH | F | H | H | H | OCH$_3$ | H | 2 | — | 0 | 0 |
| N | NH | H | H | H | H | OCH$_3$ | H | 3 | — | 0 | 0 |
| N | NH | F | H | H | H | OCH$_3$ | H | 3 | — | 0 | 0 |

TABLE 5

Compounds of the formula I (see attached formula sheet I) where n = 0, p = 0, q = 0, R6 = N-(2-propyn-1-yl)-N'-cyanoamidino and with the following further substituent meanings:

| X | Y | R1 | R2 | R3 | R4 | R5 | R7 | m | r | t | u |
|---|---|---|---|---|---|---|---|---|---|---|---|
| CH | S | H | H | H | H | CH$_3$ | H | 2 | — | 0 | 0 |
| CH | S | F | H | H | H | CH$_3$ | H | 2 | — | 0 | 0 |
| CH | S | H | H | H | H | CH$_3$ | H | 3 | — | 0 | 0 |
| CH | S | F | H | H | H | CH$_3$ | H | 3 | — | 0 | 0 |
| CH | NH | H | H | H | H | OCH$_3$ | H | 2 | — | 0 | 0 |
| CH | NH | F | H | H | H | OCH$_3$ | H | 2 | — | 0 | 0 |
| CH | NH | H | H | H | H | OCH$_3$ | H | 3 | — | 0 | 0 |
| CH | NH | F | H | H | H | OCH$_3$ | H | 3 | — | 0 | 0 |
| N | S | H | H | H | H | CH$_3$ | H | 2 | — | 0 | 0 |
| N | S | F | H | H | H | CH$_3$ | H | 2 | — | 0 | 0 |
| N | S | H | H | H | H | CH$_3$ | H | 3 | — | 0 | 0 |
| N | S | F | H | H | H | CH$_3$ | H | 3 | — | 0 | 0 |
| N | NH | H | H | H | H | OCH$_3$ | H | 2 | — | 0 | 0 |
| N | NH | F | H | H | H | OCH$_3$ | H | 2 | — | 0 | 0 |
| N | NH | H | H | H | H | OCH$_3$ | H | 3 | — | 0 | 0 |
| N | NH | F | H | H | H | OCH$_3$ | H | 3 | — | 0 | 0 |

TABLE 6

Compounds of the formula I (see attached formula sheet I) where n = 0, p = 0, q = 0, R6 = 5,6-dihydroxy-1,3,4-triazin-2-yl and with the following further substituent meanings:

| X | Y | R1 | R2 | R3 | R4 | R5 | R7 | m | r | t | u |
|---|---|---|---|---|---|---|---|---|---|---|---|
| CH | S | H | H | H | H | CH$_3$ | H | 2 | — | 0 | 0 |
| CH | S | H | H | H | H | CH$_3$ | H | 2 | — | 0 | 0 |
| CH | S | OCH$_3$ | H | H | H | CH$_3$ | H | 2 | — | 0 | 0 |
| CH | S | F | H | H | H | CH$_3$ | H | 2 | — | 0 | 0 |

TABLE 6-continued

Compounds of the formula I (see attached formula sheet I) where n = 0, p = 0, q = 0, R6 = 5,6-dihydroxy-1,3,4-triazin-2-yl and with the following further substituent meanings:

| X | Y | R1 | R2 | R3 | R4 | R5 | R7 | m | r | t | u |
|---|---|---|---|---|---|---|---|---|---|---|---|
| CH | S | F | F | H | H | CH$_3$ | H | 2 | — | 0 | 0 |
| CH | S | H | H | H | H | CH$_3$ | H | 3 | — | 0 | 0 |
| CH | S | OCH$_3$ | H | H | H | CH$_3$ | H | 3 | — | 0 | 0 |
| CH | S | F | H | H | H | CH$_3$ | H | 3 | — | 0 | 0 |
| CH | S | F | F | H | H | CH$_3$ | H | 3 | — | 0 | 0 |
| N | S | H | H | H | H | CH$_3$ | H | 2 | — | 0 | 0 |
| N | S | OCH$_3$ | H | H | H | CH$_3$ | H | 2 | — | 0 | 0 |
| N | S | F | H | H | H | CH$_3$ | H | 2 | — | 0 | 0 |
| N | S | F | F | H | H | CH$_3$ | H | 2 | — | 0 | 0 |
| N | S | H | H | H | H | CH$_3$ | H | 3 | — | 0 | 0 |
| N | S | OCH$_3$ | H | H | H | CH$_3$ | H | 3 | — | 0 | 0 |
| N | S | F | H | H | H | CH$_3$ | H | 3 | — | 0 | 0 |
| N | S | F | F | H | H | CH$_3$ | H | 3 | — | 0 | 0 |
| CH | SO$_2$ | H | H | H | H | CH$_3$ | H | 2 | — | 0 | 0 |
| CH | SO$_2$ | OCH$_3$ | H | H | H | CH$_3$ | H | 2 | — | 0 | 0 |
| CH | SO$_2$ | F | H | H | H | CH$_3$ | H | 2 | — | 0 | 0 |
| CH | SO$_2$ | F | F | H | H | CH$_3$ | H | 2 | — | 0 | 0 |
| CH | SO$_2$ | H | H | H | H | CH$_3$ | H | 3 | — | 0 | 0 |
| CH | SO$_2$ | OCH$_3$ | H | H | H | CH$_3$ | H | 3 | — | 0 | 0 |
| CH | SO$_2$ | F | H | H | H | CH$_3$ | H | 3 | — | 0 | 0 |
| CH | SO$_2$ | F | F | H | H | CH$_3$ | H | 3 | — | 0 | 0 |
| N | SO$_2$ | H | H | H | H | CH$_3$ | H | 2 | — | 0 | 0 |
| N | SO$_2$ | OCH$_3$ | H | H | H | CH$_3$ | H | 2 | — | 0 | 0 |
| N | SO$_2$ | F | H | H | H | CH | H | 2 | — | 0 | 0 |
| N | SO$_2$ | F | F | H | H | CH$_3$ | H | 2 | — | 0 | 0 |
| N | SO$_2$ | H | H | H | H | CH$_3$ | H | 3 | — | 0 | 0 |
| N | SO$_2$ | OCH$_3$ | H | H | H | CH$_3$ | H | 3 | — | 0 | 0 |
| N | SO$_2$ | F | H | H | H | CH$_3$ | H | 3 | — | 0 | 0 |
| N | SO$_2$ | F | F | H | H | CH$_3$ | H | 3 | — | 0 | 0 |

TABLE 7

Compounds of the formula I (see attached formula sheet I) where n = 0, p = 0, q = 0, R4 = methylsulfonyl and with the following further substituent meanings:

| X | Y | R1 | R2 | R3 | R5 | R6 | R7 | m | r | t | u |
|---|---|---|---|---|---|---|---|---|---|---|---|
| CH | S | H | H | H | CH$_3$ | Phenyl | H | 3 | — | 0 | 0 |
| CH | S | H | H | H | CH$_3$ | 3-Dimethylaminomethy-phenyl | H | 3 | — | 0 | 0 |
| CH | S | H | H | H | CH$_3$ | 3-Piperidinomethylphenyl | H | 3 | — | 0 | 0 |
| CH | S | H | H | H | CH$_3$ | 2-Thiazolyl | H | 3 | — | 0 | 0 |
| CH | S | H | H | H | CH$_3$ | 4,5-Dimethyl-2-thiazolyl | H | 3 | — | 0 | 0 |
| CH | S | H | H | H | CH$_3$ | 2-Imidazolyl | H | 3 | — | 0 | 0 |
| CH | S | H | H | H | CH$_3$ | 1-Methyl-2-imidazolyl | H | 3 | — | 0 | 0 |
| CH | S | H | H | H | CH$_3$ | 1,2,3-Triazol-4-yl | H | 3 | — | 0 | 0 |
| CH | S | H | H | H | CH$_3$ | 1-Methyl-1,2,3-triazol-4-yl | H | 3 | — | 0 | 0 |
| CH | S | H | H | H | CH$_3$ | 1,2,4-Triazol-3-yl | H | 3 | — | 0 | 0 |
| CH | S | H | H | H | CH$_3$ | 4-Methyl-1,2,4-triazol-3-yl | H | 3 | — | 0 | 0 |
| CH | S | H | H | H | CH$_3$ | Tetrazol-5-yl | H | 3 | — | 0 | 0 |
| CH | S | H | H | H | CH$_3$ | 1-Methyltetrazol-5-yl | H | 3 | — | 0 | 0 |
| CH | S | H | H | H | CH$_3$ | 1-(2-Dimethlyaminoethyl)tetrazol-5-yl | H | 3 | — | 0 | 0 |
| CH | S | H | H | H | CH$_3$ | 1-(2-Hydroxyethyl)tetrazol-5-yl | H | 3 | — | 0 | 0 |
| CH | S | H | H | H | CH$_3$ | 1,2,3-Thiadiazol-4-yl | H | 3 | — | 0 | 0 |
| CH | S | H | H | H | CH$_3$ | 1,3,4-Thiadiazol-2-yl | H | 3 | — | 0 | 0 |
| CH | S | H | H | H | CH$_3$ | 2-Methyl-1,3,4-thiadiazol-2-yl | H | 3 | — | 0 | 0 |
| CH | S | H | H | H | CH$_3$ | 2-Pyridinyl | H | 3 | — | 0 | 0 |
| CH | S | H | H | H | CH$_3$ | 4-Pyridinyl | H | 3 | — | 0 | 0 |
| CH | S | H | H | H | CH$_3$ | 2-Pyrimidinyl | H | 3 | — | 0 | 0 |
| CH | S | H | H | H | CH$_3$ | 2-Benzimidazolyl | H | 3 | — | 0 | 0 |
| CH | S | H | H | H | CH$_3$ | 5,6-Dihydroxy-1,3,4-triazin-2-yl | H | 3 | — | 0 | 0 |

TABLE 8

Compounds of the formula I (see attached formula sheet I)
where n = 0, p = 0, q = 0, R4 = H and
with the following further substituent meanings:

| X | Y | R1 | R2 | R3 | R5 | R6 | R7 | m | r | t | u |
|---|---|----|----|----|-----|----|----|---|---|---|---|
| CH | O | H | H | H | CH₃ | Phenyl | H | 3 | — | 0 | 0 |
| CH | O | H | H | H | CH₃ | 3-Dimethylaminomethylphenyl | H | 3 | — | 0 | 0 |
| CH | O | H | H | H | CH₃ | 3-Piperidinomethylphenyl | H | 3 | — | 0 | 0 |
| CH | O | H | H | H | CH₃ | 2-Pyridinyl | H | 3 | — | 0 | 0 |
| CH | O | H | H | H | CH₃ | 4-Pyridinyl | H | 3 | — | 0 | 0 |
| CH | O | H | H | H | CH₃ | Phenyl | H | 2 | — | 0 | 0 |
| CH | O | H | H | H | CH₃ | 3-Dimethylaminomethylphenyl | H | 2 | — | 0 | 0 |
| CH | O | H | H | H | CH₃ | 3-Piperidinomethylphenyl | H | 2 | — | 0 | 0 |
| CH | O | H | H | H | CH₃ | 2-Pyridinyl | H | 2 | — | 0 | 0 |
| CH | O | H | H | H | CH₃ | 4-Pyridinyl | H | 2 | — | 0 | 0 |
| CH | O | H | H | H | CH₃ | Phenyl | H | 4 | — | 0 | 0 |
| CH | O | H | H | H | CH₃ | 3-Dimethylaminomethylphenyl | H | 4 | — | 0 | 0 |
| CH | O | H | H | H | CH₃ | 3-Piperidinomethylphenyl | H | 4 | — | 0 | 0 |
| CH | O | H | H | H | CH₃ | 2-Pyridinyl | H | 4 | — | 0 | 0 |
| CH | O | H | H | H | CH₃ | 4-Pyridinyl | H | 4 | — | 0 | 0 |

TABLE 9

Compounds of the formula I (see attached formula sheet I)
where n = 0, p = 0, q = 0, R4 = H and
with the following further substituent meanings:

| X | Y | R1 | R2 | R3 | R5 | R6 | R7 | m | r | t | u |
|---|---|----|----|----|-----|----|----|---|---|---|---|
| N | S | H | H | H | CH₃ | Phenyl | H | 3 | — | 0 | 0 |
| N | S | H | H | H | CH₃ | 3-Dimethylaminomethylphenyl | H | 3 | — | 0 | 0 |
| N | S | H | H | H | CH₃ | 3-Piperidinomethylphenyl | H | 3 | — | 0 | 0 |
| N | S | H | H | H | CH₃ | 2-Thiazolyl | H | 3 | — | 0 | 0 |
| N | S | H | H | H | CH₃ | 4,5-Dimethyl-2-thiazolyl | H | 3 | — | 0 | 0 |
| N | S | H | H | H | CH₃ | 2-Imidazolyl | H | 3 | — | 0 | 0 |
| N | S | H | H | H | CH₃ | 1-Methyl-2-imidazolyl | H | 3 | — | 0 | 0 |
| N | S | H | H | H | CH₃ | 1,2,3-Triazol-4-yl | H | 3 | — | 0 | 0 |
| N | S | H | H | H | CH₃ | 1-Methyl-1,2,3-triazo1-4-yl | H | 3 | — | 0 | 0 |
| N | S | H | H | H | CH₃ | 1,2,4-Triazol-3-yl | H | 3 | — | 0 | 0 |
| N | S | H | H | H | CH₃ | 4-Methyl-1,2,4-triazol-3-yl | H | 3 | — | 0 | 0 |
| N | S | H | H | H | CH₃ | Tetrazol-5-yl | H | 3 | — | 0 | 0 |
| N | S | H | H | H | CH₃ | 1-Methyltetrazol-5-yl | H | 3 | — | 0 | 0 |
| N | S | H | H | H | CH₃ | 1-(2-Dimethylaminoethyl)tetrazol-5-yl | H | 3 | — | 0 | 0 |
| N | S | H | H | H | CH₃ | 1-(2-Hydroxyethyl)tetrazol-5-yl | H | 3 | — | 0 | 0 |
| N | S | H | H | H | CH₃ | 1,2,3-Thiadiazol-4-yl | H | 3 | — | 0 | 0 |
| N | S | H | H | H | CH₃ | 1,3,4-Thiadiazol-2-yl | H | 3 | — | 0 | 0 |
| N | S | H | H | H | CH₃ | 5-Methyl-1,3,4-thiadiazol-2-yl | H | 3 | — | 0 | 0 |
| N | S | H | H | H | CH₃ | 2-Pyridinyl | H | 3 | — | 0 | 0 |
| N | S | H | H | H | CH₃ | 4-Pyridinyl | H | 3 | — | 0 | 0 |
| N | S | H | H | H | CH₃ | 2-Pyrimidinyl | H | 3 | — | 0 | 0 |
| N | S | H | H | H | CH₃ | 2-Benzimidazolyl | H | 3 | — | 0 | 0 |
| N | S | H | H | H | CH₃ | 5,6-Dihydroxy-1,3,4-triazin-2-yl | H | 3 | — | 0 | 0 |

TABLE 10

Compounds of the formula I (see attached formula sheet I)
where n = 0, p = 0, q = 0, R4 = H and
with the following further substituent meanings:

| X | Y | R1 | R2 | R3 | R5 | R6 | R7 | m | r | t | u |
|---|---|----|----|----|-----|----|----|---|---|---|---|
| CH | S | H | H | H | CH₃ | Phenyl | H | 3 | — | 0 | 1 |
| CH | S | H | H | H | CH₃ | 3-Dimethylaminomethylphenyl | H | 3 | — | 0 | 1 |
| CH | S | H | H | H | CH₃ | 3-Piperidinomethylphenyl | H | 3 | — | 0 | 1 |
| CH | S | H | H | H | CH₃ | 2-Thiazolyl | H | 3 | — | 0 | 1 |
| CH | S | H | H | H | CH₃ | 4,5-Dimethyl-2-thiazolyl | H | 3 | — | 0 | 1 |
| CH | S | H | H | H | CH₃ | 2-Imidazolyl | H | 3 | — | 0 | 1 |
| CH | S | H | H | H | CH₃ | 1-Methyl-2-imidazolyl | H | 3 | — | 0 | 1 |
| CH | S | H | H | H | CH₃ | 1,2,3-Triazol-4-yl | H | 3 | — | 0 | 1 |
| CH | S | H | H | H | CH₃ | 1-Methyl-1,2,3-triazol-4-yl | H | 3 | — | 0 | 1 |
| CH | S | H | H | H | CH₃ | 1,2,4-Triazol-3-yl | H | 3 | — | 0 | 1 |
| CH | S | H | H | H | CH₃ | 4-Methyl-1,2,4-triazol-3-yl | H | 3 | — | 0 | 1 |
| CH | S | H | H | H | CH₃ | Tetrazol-5-yl | H | 3 | — | 0 | 1 |

TABLE 10-continued

Compounds of the formula I (see attached formula sheet I) where n = 0, p = 0, q = 0, R4 = H and with the following further substituent meanings:

| X | Y | R1 | R2 | R3 | R5 | R6 | R7 | m | r | t | u |
|---|---|---|---|---|---|---|---|---|---|---|---|
| CH | S | H | H | H | CH₃ | 1-Methyltetrazol-5-yl | H | 3 | — | 0 | 1 |
| CH | S | H | H | H | CH₃ | 1-(2-Dimethylaminoethyl)tetrazol-5-yl | H | 3 | — | 0 | 1 |
| CH | S | H | H | H | CH₃ | 1-(2-Hydroxyethyl)tetrazol-5-yl | H | 3 | — | 0 | 1 |
| CH | S | H | H | H | CH₃ | 1,2,3-Thiadiazol-4-yl | H | 3 | — | 0 | 1 |
| CH | S | H | H | H | CH₃ | 1,3,4-Thiadiazol-2-yl | H | 3 | — | 0 | 1 |
| CH | S | H | H | H | CH₃ | 5-Methyl-1,3,4-thiadiazol-2-yl | H | 3 | — | 0 | 1 |
| CH | S | H | H | H | CH₃ | 2-Pyridinyl | H | 3 | — | 0 | 1 |
| CH | S | H | H | H | CH₃ | 4-Pyridinyl | H | 3 | — | 0 | 1 |
| CH | S | H | H | H | CH₃ | 2-Pyrimidinyl | H | 3 | — | 0 | 1 |
| CH | S | H | H | H | CH₃ | 2-Benzimidazolyl | H | 3 | — | 0 | 1 |
| CH | S | H | H | H | CH₃ | 2-Furanyl | H | 3 | — | 0 | 1 |
| CH | S | H | H | H | CH₃ | 2-Thienyl | H | 3 | — | 0 | 1 |
| CH | S | H | H | H | CH₃ | 5-Chloro-thiophen-2-yl | H | 3 | — | 0 | 1 |
| CH | S | H | H | H | CH₃ | 5-(2-Dimethylaminomethyl)furan-2-yl | H | 3 | — | 0 | 1 |
| CH | S | H | H | H | CH₃ | 5-Methyl-furan-2-yl | H | 3 | — | 0 | 1 |

TABLE 11

Compounds of the formula I (see attached formula sheet I) where n = 0, p = 0, q = 0, R4 = H and with the following further substituent meanings:

| X | Y | R1 | R2 | R3 | R5 | R6 | R7 | m | r | t | u |
|---|---|---|---|---|---|---|---|---|---|---|---|
| CH | SO₂ | H | H | H | CH₃ | Phenyl | H | 3 | — | 0 | 2 |
| CH | SO₂ | H | H | H | CH₃ | 3-Dimethylaminomethylphenyl | H | 3 | — | 0 | 2 |
| CH | SO₂ | H | H | H | CH₃ | 3-Piperidinomethylphenyl | H | 3 | — | 0 | 2 |
| CH | SO₂ | H | H | H | CH₃ | 2-Thiazolyl | H | 3 | — | 0 | 2 |
| CH | SO₂ | H | H | H | CH₃ | 4,5-Dimethyl-2-thiazolyl | H | 3 | — | 0 | 2 |
| CH | SO₂ | H | H | H | CH₃ | 2-Imidazolyl | H | 3 | — | 0 | 2 |
| CH | SO₂ | H | H | H | CH₃ | 1-Methyl-2-imidazolyl | H | 3 | — | 0 | 2 |
| CH | SO₂ | H | H | H | CH₃ | 1,2,3-Triazol-4-yl | H | 3 | — | 0 | 2 |
| CH | SO₂ | H | H | H | CH₃ | 1-Methyl-1,2,3-triazol-4-yl | H | 3 | — | 0 | 2 |
| CH | SO₂ | H | H | H | CH₃ | 1,2,4-Triazol-3-yl | H | 3 | — | 0 | 2 |
| CH | SO₂ | H | H | H | CH₃ | 4-Methyl-1,2,4-triazol-3-yl | H | 3 | — | 0 | 2 |
| CH | SO₂ | H | H | H | CH₃ | Tetrazol-5-yl | H | 3 | — | 0 | 2 |
| CH | SO₂ | H | H | H | CH₃ | 1-Methyltetrazol-5-yl | H | 3 | — | 0 | 2 |
| CH | SO₂ | H | H | H | CH₃ | 1-(2-Dimethylaminoethyl)tetrazol-5-yl | H | 3 | — | 0 | 2 |
| CH | SO₂ | H | H | H | CH₃ | 1-(2-Hydroxyethyl)tetrazol-5-yl | H | 3 | — | 0 | 2 |
| CH | SO₂ | H | H | H | CH₃ | 1,2,3-Thiadiazol-4-yl | H | 3 | — | 0 | 2 |
| CH | SO₂ | H | H | H | CH₃ | 1,3,4-Thiadiazol-2-yl | H | 3 | — | 0 | 2 |
| CH | SO₂ | H | H | H | CH₃ | 5-Methyl-1,3,4-thiadiazol-2-yl | H | 3 | — | 0 | 2 |
| CH | SO₂ | H | H | H | CH₃ | 2-Pyridinyl | H | 3 | — | 0 | 2 |
| CH | SO₂ | H | H | H | CH₃ | 4-Pyridinyl | H | 3 | — | 0 | 2 |
| CH | SO₂ | H | H | H | CH₃ | 2-Pyrimidinyl | H | 3 | — | 0 | 2 |
| CH | SO₂ | H | H | H | CH₃ | 2-Benzimidazolyl | H | 3 | — | 0 | 2 |
| CH | SO₂ | H | H | H | CH₃ | 2-Furanyl | H | 3 | — | 0 | 2 |
| CH | SO₂ | H | H | H | CH₃ | 2-Thienyl | H | 3 | — | 0 | 2 |
| CH | SO₂ | H | H | H | CH₃ | 5-Chloro-thiophen-2-yl | H | 3 | — | 0 | 2 |
| CH | SO₂ | H | H | H | CH₃ | 5-(2-Dimethylaminomethyl)furan-2-yl | H | 3 | — | 0 | 2 |
| CH | SO₂ | H | H | H | CH₃ | 5-Methyl-furan-2-yl | H | 3 | — | 0 | 2 |

TABLE 12

Compounds of the formula I (see attached formula sheet I) where n = 0, p = 0, q = 0, R4 = H and with the following further substituent meanings:

| X | Y | R1 | R2 | R3 | R5 | R6 | R7 | m | r | t | u |
|---|---|---|---|---|---|---|---|---|---|---|---|
| CH | S | OCH₃ | H | H | CH₃ | Phenyl | H | 3 | — | 0 | 1 |
| CH | S | OCH₃ | H | H | CH₃ | 3-Dimethylaminomethylphenyl | H | 3 | — | 0 | 1 |
| CH | S | OCH₃ | H | H | CH₃ | 3-Piperidinomethylphenyl | H | 3 | — | 0 | 1 |
| CH | S | OCH₃ | H | H | CH₃ | 2-Thiazolyl | H | 3 | — | 0 | 1 |
| CH | S | OCH₃ | H | H | CH₃ | 4,5-Dimethyl-2-thiazolyl | H | 3 | — | 0 | 1 |
| CH | S | OCH₃ | H | H | CH₃ | 2-Imidaiolyl | H | 3 | — | 0 | 1 |
| CH | S | OCH₃ | H | H | CH₃ | 1-Methyl-2-imidazolyl | H | 3 | — | 0 | 1 |
| CH | S | OCH₃ | H | H | CH₃ | 1,2,3-Triazol-4-yl | H | 3 | — | 0 | 1 |

TABLE 12-continued

Compounds of the formula I (see attached formula sheet I)
where n = 0, p = 0, q = 0, R4 = H and
with the following further substituent meanings:

| X | Y | R1 | R2 | R3 | R5 | R6 | R7 | m | r | t | u |
|---|---|---|---|---|---|---|---|---|---|---|---|
| CH | S | OCH$_3$ | H | H | CH$_3$ | 1-Methyl-1,2,3-triazol-4-yl | H | 3 | — | 0 | 1 |
| CH | S | OCH$_3$ | H | H | CH$_3$ | 3,2,4-Triazol-3-yl | H | 3 | — | 0 | 1 |
| CH | S | OCH$_3$ | H | H | CH$_3$ | 4-Methyl-1,2,4-triazol-3-yl | H | 3 | — | 0 | 1 |
| CH | S | OCH$_3$ | H | H | CH$_3$ | Tetrazol-5-yl | H | 3 | — | 0 | 1 |
| CH | S | OCH$_3$ | H | H | CH$_3$ | 1-Methyltetrazol-5-yl | H | 3 | — | 0 | 1 |
| CH | S | OCH$_3$ | H | H | CH$_3$ | 1-(2-Dimethylaminoethyl)tetrazol-5-yl | H | 3 | — | 0 | 1 |
| CH | S | OCH$_3$ | H | H | CH$_3$ | 3-(2-Hydroxyethyl)tetrazol-5-yl | H | 3 | — | 0 | 1 |
| CH | S | OCH$_3$ | H | H | CH$_3$ | 1,2,3-Thiadiazol-4-yl | H | 3 | — | 0 | 1 |
| CH | S | OCH$_3$ | H | H | CH$_3$ | 1,3,4-Thiadiazol-2-yl | H | 3 | — | 0 | 1 |
| CH | S | OCH$_3$ | H | H | CH$_3$ | 5-Methyl-1,3,4-thiadiazol-2-yl | H | 3 | — | 0 | 1 |
| CH | S | OCH$_3$ | H | H | CH$_3$ | 2-Pyridinyl | H | 3 | — | 0 | 1 |
| CH | S | OCH$_3$ | H | H | CH$_3$ | 4-Pyridinyl | H | 3 | — | 0 | 1 |
| CH | S | OCH$_3$ | H | H | CH$_3$ | 2-Pyrimidinyl | H | 3 | — | 0 | 1 |
| CH | S | OCH$_3$ | H | H | CH$_3$ | 2-Benzimidazolyl | H | 3 | — | 0 | 1 |
| CH | S | OCH$_3$ | H | H | CH$_3$ | 2-Furanyl | H | 3 | — | 0 | 1 |
| CH | S | OCH$_3$ | H | H | CH$_3$ | 2-Thienyl | H | 3 | — | 0 | 1 |
| CH | S | OCH$_3$ | H | H | CH$_3$ | 5-Chloro-thiophen-2-yl | H | 3 | — | 0 | 1 |
| CH | S | OCH$_3$ | H | H | CH$_3$ | 5-(2-Dimethylaminomethyl)furan-2-yl | H | 3 | — | 0 | 1 |
| CH | S | OCH$_3$ | H | H | CH$_3$ | 5-Methyl-furan-2-yl | H | 3 | — | 0 | 1 |

TABLE 13

Compounds of the formula I (see attached formula sheet I)
where n = 0, p = 0, q = 0, R4 = H and
with the following further substituent meanings:

| X | Y | R1 | R2 | R3 | R5 | R6 | R7 | m | r | t | u |
|---|---|---|---|---|---|---|---|---|---|---|---|
| CH | S | F | H | H | CH$_3$ | Phenyl | H | 3 | — | 0 | 1 |
| CH | S | F | H | H | CH$_3$ | 3-Dimethylaminomethylphenyl | H | 3 | — | 0 | 1 |
| CH | S | F | H | H | CH$_3$ | 3-Piperidinomethylphenyl | H | 3 | — | 0 | 1 |
| CH | S | F | H | H | CH$_3$ | 2-Thiazolyl | H | 3 | — | 0 | 1 |
| CH | S | F | H | H | CH$_3$ | 4,5-Dimethyl-2-thiazolyl | H | 3 | — | 0 | 1 |
| CH | S | F | H | H | CH$_3$ | 2-Imidazolyl | H | 3 | — | 0 | 1 |
| CH | S | F | H | H | CH$_3$ | 1-Methyl-2-imidazolyl | H | 3 | — | 0 | 1 |
| CH | S | F | H | H | CH$_3$ | 1,2,3-Triazol-4-yl | H | 3 | — | 0 | 1 |
| CH | S | F | H | H | CH$_3$ | 1-Methyl-1,2,3-triazol-4-yl | H | 3 | — | 0 | 1 |
| CH | S | F | H | H | CH$_3$ | 1,2,4-Triazol-3-yl | H | 3 | — | 0 | 1 |
| CH | S | F | H | H | CH$_3$ | 4-Methyl-1,2,4-triazol-3-yl | H | 3 | — | 0 | 1 |
| CH | S | F | H | H | CH$_3$ | Tetrazol-5-yl | H | 3 | — | 0 | 1 |
| CH | S | F | H | H | CH$_3$ | 1-Methyltetrazol-5-yl | H | 3 | — | 0 | 1 |
| CH | S | F | H | H | CH$_3$ | 1-(2-Dimethy-aminoethyl)tetrazol-5-yl | H | 3 | — | 0 | 1 |
| CH | S | F | H | H | CH$_3$ | 1-(2-Hydroxyethyl)tetrazol-5-yl | H | 3 | — | 0 | 1 |
| CH | S | F | H | H | CH$_3$ | 1,2,3-Thiadiazol-4-yl | H | 3 | — | 0 | 1 |
| CH | S | F | H | H | CH$_3$ | 1,3,4-Thiadiazol-2-yl | H | 3 | — | 0 | 1 |
| CH | S | F | H | H | CH$_3$ | 5-Methyl-1,3,4-thiadiazol-2-yl | H | 3 | — | 0 | 1 |
| CH | S | F | H | H | CH$_3$ | 2-Pyridinyl | H | 3 | — | 0 | 1 |
| CH | S | F | H | H | CH$_3$ | 4-Pyridinyl | H | 3 | — | 0 | 1 |
| CH | S | F | H | H | CH$_3$ | 2-Pyrimidinyl | H | 3 | — | 0 | 1 |
| CH | S | F | H | H | CH$_3$ | 2-Benzimidazolyl | H | 3 | — | 0 | 1 |
| CH | S | F | H | H | CH$_3$ | 2-Furanyl | H | 3 | — | 0 | 1 |
| CH | S | F | H | H | CH$_3$ | 2-Thienyl | H | 3 | — | 0 | 1 |
| CH | S | F | H | H | CH$_3$ | 5-Chloro-thiophen-2-yl | H | 3 | — | 0 | 1 |
| CH | S | F | H | H | CH$_3$ | 5-(2-Dimethylaminomethyl)furan-2-yl | H | 3 | — | 0 | 1 |
| CH | S | F | H | H | CH$_3$ | 5-Methyl-furan-2-yl | H | 3 | — | 0 | 1 |

TABLE 14

Compounds of the formula I (see attached formula sheet I)
where n = 0, p = 0, q = 0, R4 = H and
with the following further substituent meanings:

| X | Y | R1 | R2 | R3 | R5 | R6 | R7 | m | r | t | u |
|---|---|---|---|---|---|---|---|---|---|---|---|
| CH | S | H | H | H | CH$_3$ | Phenyl | H | 3 | — | 0 | 2 |
| CH | S | H | H | H | CH$_3$ | 3-Dimethylaminomethylphenyl | H | 3 | — | 0 | 2 |
| CH | S | H | H | H | CH$_3$ | 3-Piperidinomethylphenyl | H | 3 | — | 0 | 2 |
| CH | S | H | H | H | CH$_3$ | 2-Thiazolyl | H | 3 | — | 0 | 2 |

TABLE 14-continued

Compounds of the formula I (see attached formula sheet I)
where n = 0, p = 0, q = 0, R4 = H and
with the following further substituent meanings:

| X | Y | R1 | R2 | R3 | R5 | R6 | R7 | m | r | t | u |
|---|---|---|---|---|---|---|---|---|---|---|---|
| CH | S | H | H | H | CH₃ | 4,5-Dimethyl-2-thiazolyl | H | 3 | — | 0 | 2 |
| CH | S | H | H | H | CH₃ | 2-Imidazolyl | H | 3 | — | 0 | 2 |
| CH | S | H | H | H | CH₃ | 1-Methyl-2-imidazolyl | H | 3 | — | 0 | 2 |
| CH | S | H | H | H | CH₃ | 1,2,3-Triazol-4-yl | H | 3 | — | 0 | 2 |
| CH | S | H | H | H | CH₃ | 1-Methyl-1,2,3-triazol-4-yl | H | 3 | — | 0 | 2 |
| CH | S | H | H | H | CH₃ | 1,2,4-Triazol-3-yl | H | 3 | — | 0 | 2 |
| CH | S | H | H | H | CH₃ | 4-Methyl-1,2,4-triazol-3-yl | H | 3 | — | 0 | 2 |
| CH | S | H | H | H | CH₃ | Tetrazol-5-yl | H | 3 | — | 0 | 2 |
| CH | S | H | H | H | CH₃ | 1-Methyltetrazol-5-yl | H | 3 | — | 0 | 2 |
| CH | S | H | H | H | CH₃ | 1-(2-Dimethylaminoethyl)tetrazol-5-yl | H | 3 | — | 0 | 2 |
| CH | S | H | H | H | CH₃ | 1-(2-Hydroxyethyl)tetrazol-5-yl | H | 3 | — | 0 | 2 |
| CH | S | H | H | H | CH₃ | 1,2,3-Thiadiazol-4-yl | H | 3 | — | 0 | 2 |
| CH | S | H | H | H | CH₃ | 1,3,4-Thiadiazol-2-yl | H | 3 | — | 0 | 2 |
| CH | S | H | H | H | CH₃ | 5-Methyl-1,3,4-thiadiazol-2-yl | H | 3 | — | 0 | 2 |
| CH | S | H | H | H | CH₃ | 2-Pyridinyl | H | 3 | — | 0 | 2 |
| CH | S | H | H | H | CH₃ | 4-Pyridinyl | H | 3 | — | 0 | 2 |
| CH | S | H | H | H | CH₃ | 2-Pyrimidinyl | H | 3 | — | 0 | 2 |
| CH | S | H | H | H | CH₃ | 2-Benzimidazolyl | H | 3 | — | 0 | 2 |
| CH | S | H | H | H | CH₃ | 5-Nitroimidazol-1-yl | H | 3 | — | 0 | 2 |
| CH | S | H | H | H | CH₃ | 2-Methyl-5-nitroimidazol-1-yl | H | 3 | — | 0 | 2 |
| CH | S | H | H | H | CH₃ | 2-Furanyl | H | 3 | — | 0 | 2 |
| CH | S | H | H | H | CH₃ | 2-Thienyl | H | 3 | — | 0 | 2 |
| CH | S | H | H | H | CH₃ | 5-Chloro-thiophen-2-yl | H | 3 | — | 0 | 2 |
| CH | S | H | H | H | CH₃ | 5-(2-Dimethylaminomethyl)furan-2-yl | H | 3 | — | 0 | 2 |
| CH | S | H | H | H | CH₃ | 5-Methyl-furan-2-yl | H | 3 | — | 0 | 2 |

TABLE 15

Compounds of the formula I (see attached formula sheet I)
where n = 0, p = 0, q = 0, R4 = H and
with the following further substituent meanings:

| X | Y | R1 | R2 | R3 | R5 | R6 | R7 | m | r | t | u |
|---|---|---|---|---|---|---|---|---|---|---|---|
| CH | S | H | H | H | CH₃ | Phenyl | H | 3 | 3 | 1 | 0 |
| CH | S | H | H | H | CH₃ | 3-Dimethylaminomethylphenyl | H | 3 | 3 | 1 | 0 |
| CH | S | H | H | H | CH₃ | 3-Piperidinomethylphenyl | H | 3 | 3 | 1 | 0 |
| CH | S | H | H | H | CH₃ | 2-Thiazolyl | H | 3 | 3 | 1 | 0 |
| CH | S | H | H | H | CH₃ | 4,5-Dimethyl-2-thiazolyl | H | 3 | 3 | 1 | 0 |
| CH | S | H | H | H | CH₃ | 2-Imidazolyl | H | 3 | 3 | 1 | 0 |
| CH | S | H | H | H | CH₃ | 1-Methyl-2-imidazolyl | H | 3 | 3 | 1 | 0 |
| CH | S | H | H | H | CH₃ | 1,2,3-Triazol-4-yl | H | 3 | 3 | 1 | 0 |
| CH | S | H | H | H | CH₃ | 1-Methyl-1,2,3-triazol-4-yl | H | 3 | 3 | 1 | 0 |
| CH | S | H | H | H | CH₃ | 1,2,4-Triazol-3-yl | H | 3 | 3 | 1 | 0 |
| CH | S | H | H | H | CH₃ | 4-Methyl-1,2,4-triazol-3-yl | H | 3 | 3 | 1 | 0 |
| CH | S | H | H | H | CH₃ | Tetrazol-5-yl | H | 3 | 3 | 1 | 0 |
| CH | S | H | H | H | CH₃ | 1-Methyltetrazol-5-yl | H | 3 | 3 | 1 | 0 |
| CH | S | H | H | H | CH₃ | 1-(2-Dimethylaminoethyl)tetrazol-5-yl | H | 3 | 3 | 1 | 0 |
| CH | S | H | H | H | CH₃ | 1-(2-Hydroxyethyl)tetrazol-5-yl | H | 3 | 3 | 1 | 0 |
| CH | S | H | H | H | CH₃ | 1,2,3-Thiadiazol-4-yl | H | 3 | 3 | 1 | 0 |
| CH | S | H | H | H | CH₃ | 1,3,4-Thiadiazol-2-yl | H | 3 | 3 | 1 | 0 |
| CH | S | H | H | H | CH₃ | 5-Methyl-1,3,4-thiadiazol-2-yl | H | 3 | 3 | 1 | 0 |
| CH | S | H | H | H | CH₃ | 2-Pyridinyl | H | 3 | 3 | 1 | 0 |
| CH | S | H | H | H | CH₃ | 4-Pyridinyl | H | 3 | 3 | 1 | 0 |
| CH | S | H | H | H | CH₃ | 2-Pyrimidinyl | H | 3 | 3 | 1 | 0 |
| CH | S | H | H | H | CH₃ | 2-Benzimidazolyl | H | 3 | 3 | 1 | 0 |
| CH | S | H | H | H | CH₃ | 5,6-Dihydroxy-1,3,4-triazin-2-yl | H | 3 | 3 | 1 | 0 |

TABLE 16

Compounds of the formula I (see attached formula sheet I) where n = 0, p = 0, q = 0, R4 = H and with the following further substituent meanings:

| X | Y | R1 | R2 | R3 | R5 | R6 | R7 | m | r | t | u |
|---|---|----|----|----|----|----|----|---|---|---|---|
| CH | S | H | H | H | CH₃ | Phenyl | H | 2 | 2 | 1 | 2 |
| CH | S | H | H | H | CH₃ | 3-Dimethylaminomethylphenyl | H | 2 | 2 | 1 | 2 |
| CH | S | H | H | H | CH₃ | 3-Piperidinomethylphenyl | H | 2 | 2 | 1 | 2 |
| CH | S | H | H | H | CH₃ | 2-Thiazolyl | H | 2 | 2 | 1 | 2 |
| CH | S | H | H | H | CH₃ | 4,5-Dimethyl-2-thiazolyl | H | 2 | 2 | 1 | 2 |
| CH | S | H | H | H | CH₃ | 2-Imidazolyl | H | 2 | 2 | 1 | 2 |
| CH | S | H | H | H | CH₃ | 1-Methyl-2-imidazolyl | H | 2 | 2 | 1 | 2 |
| CH | S | H | H | H | CH₃ | 1,2,3-Triazol-4-yl | H | 2 | 2 | 1 | 2 |
| CH | S | H | H | H | CH₃ | 1-Methyl-1,2,3-triazol-4-yl | H | 2 | 2 | 1 | 2 |
| CH | S | H | H | H | CH₃ | 1,2,4-Triazol-3-yl | H | 2 | 2 | 1 | 2 |
| CH | S | H | H | H | CH₃ | 4-Methyl-1,2,4-triazol-3-yl | H | 2 | 2 | 1 | 2 |
| CH | S | H | H | H | CH₃ | Tetrazol-5-yl | H | 2 | 2 | 1 | 2 |
| CH | S | H | H | H | CH₃ | 1-Methyltetrazol-5-yl | H | 2 | 2 | 1 | 2 |
| CH | S | H | H | H | CH₃ | 1-(2-Dimethylaminoethyl)tetrazol-5-yl | H | 2 | 2 | 1 | 2 |
| CH | S | H | H | H | CH₃ | 1-(2-Hydroxyethyl)tetrazol-5-yl | H | 2 | 2 | 1 | 2 |
| CH | S | H | H | H | CH₃ | 1,2,3-Thiadiazol-4-yl | H | 2 | 2 | 1 | 2 |
| CH | S | H | H | H | CH₃ | 1,3,4-Thiadiazol-2-yl | H | 2 | 2 | 1 | 2 |
| CH | S | H | H | H | CH₃ | 5-Methyl-1,3,4-thiadiazol-2-yl | H | 2 | 2 | 1 | 2 |
| CH | S | H | H | H | CH₃ | 2-Pyridinyl | H | 2 | 2 | 1 | 2 |
| CH | S | H | H | H | CH₃ | 4-Pyridinyl | H | 2 | 2 | 1 | 2 |
| CH | S | H | H | H | CH₃ | 2-Pyrimidinyl | H | 2 | 2 | 1 | 2 |
| CH | S | H | H | H | CH₃ | 2-Benzimidazolyl | H | 2 | 2 | 1 | 2 |

TABLE 17

Compounds of the formula I (see attached formula sheet I) where n = 0, p = 0, q = 0, R4 = H and with the following further substituent meanings:

| X | Y | R1 | R2 | R3 | R5 | R6 | R7 | m | r | t | u |
|---|---|----|----|----|----|----|----|---|---|---|---|
| CH | S | H | H | H | CH₃ | Phenyl | H | 3 | — | 0 | 3 |
| CH | S | H | H | H | CH₃ | 3-Dimethylaminomethylphenyl | H | 3 | — | 0 | 3 |
| CH | S | H | H | H | CH₃ | 3-Piperidinomethylphenyl | H | 3 | — | 0 | 3 |
| CH | S | H | H | H | CH₃ | 2-Thiazolyl | H | 3 | — | 0 | 3 |
| CH | S | H | H | H | CH₃ | 4,5-Dimethyl-2-thiazolyl | H | 3 | — | 0 | 3 |
| CH | S | H | H | H | CH₃ | 2-Imidazolyl | H | 3 | — | 0 | 3 |
| CH | S | H | H | H | CH₃ | 1-Methyl-2-imidazolyl | H | 3 | — | 0 | 3 |
| CH | S | H | H | H | CH₃ | 1,2,3-Triazol-4-yl | H | 3 | — | 0 | 3 |
| CH | S | H | H | H | CH₃ | 1-Methyl-1,2,3-triazol-4-yl | H | 3 | — | 0 | 3 |
| CH | S | H | H | H | CH₃ | 1,2,4-Triazol-3-yl | H | 3 | — | 0 | 3 |
| CH | S | H | H | H | CH₃ | 4-Methyl-1,2,4-triazol-3-yl | H | 3 | — | 0 | 3 |
| CH | S | H | H | H | CH₃ | Tetrazol-5-yl | H | 3 | — | 0 | 3 |
| CH | S | H | H | H | CH₃ | 1-Methyltetrazol-5-yl | H | 3 | — | 0 | 3 |
| CH | S | H | H | H | CH₃ | 1-(2-Dimethylaminoethyl)tetrazol-5-yl | H | 3 | — | 0 | 3 |
| CH | S | H | H | H | CH₃ | 1-(2-Hydroxyethyl)tetrazol-5-yl | H | 3 | — | 0 | 3 |
| CH | S | H | H | H | CH₃ | 1,2,3-Thiadiazol-4-yl | H | 3 | — | 0 | 3 |
| CH | S | H | H | H | CH₃ | 1,3,4-Thiadiazol-2-yl | H | 3 | — | 0 | 3 |
| CH | S | H | H | H | CH₃ | 5-Methyl-1,3,4-thiadiazol-2-yl | H | 3 | — | 0 | 3 |
| CH | S | H | H | H | CH₃ | 2-Pyridinyl | H | 3 | — | 0 | 3 |
| CH | S | H | H | H | CH₃ | 4-Pyridinyl | H | 3 | — | 0 | 3 |
| CH | S | H | H | H | CH₃ | 2-Pyrimidinyl | H | 3 | — | 0 | 3 |
| CH | S | H | H | H | CH₃ | 2-Benzimidazolyl | H | 3 | — | 0 | 3 |
| CH | S | H | H | H | CH₃ | 5-Nitroimidazol-1-yl | H | 3 | — | 0 | 3 |
| CH | S | H | H | H | CH₃ | 2-Methyl-5-nitromidazol-1-yl | H | 3 | — | 0 | 3 |
| CH | S | H | H | H | CH₃ | 2-Furanyl | H | 3 | — | 0 | 3 |
| CH | S | H | H | H | CH₃ | 2-Thienyl | H | 3 | — | 0 | 3 |
| CH | S | H | H | H | CH₃ | 5-Chloro-thiophen-2-yl | H | 3 | — | 0 | 3 |
| CH | S | H | H | H | CH₃ | 5-(2-Dimethylaminomethyl)furan-2-yl | H | 3 | — | 0 | 3 |
| CH | S | H | H | H | CH₃ | 5-Methyl-furan-2-yl | H | 3 | — | 0 | 3 |

TABLE 18

Compounds of the formula I (see attached formula sheet I)
where n = 0 , p = 0, q = 0, R4 = H and
with the following further substituent meanings:

| X | Y | R1 | R2 | R3 | R5 | R6 | R7 | m | r | t | u |
|---|---|----|----|----|----|----|----|----|----|----|----|
| N | S | H | H | H | $CH_3$ | Phenyl | H | 3 | — | 0 | 1 |
| N | S | H | H | H | $CH_3$ | 3-Dimethylaminomethylphenyl | H | 3 | — | 0 | 1 |
| N | S | H | H | H | $CH_3$ | 3-Piperidinomethylphenyl | H | 3 | — | 0 | 1 |
| N | S | H | H | H | $CH_3$ | 2-Thiazolyl | H | 3 | — | 0 | 1 |
| N | S | H | H | H | $CH_3$ | 4,5-Dimethyl-2-thiazolyl | H | 3 | — | 0 | 1 |
| N | S | H | H | H | $CH_3$ | 2-Imidazolyl | H | 3 | — | 0 | 1 |
| N | S | H | H | H | $CH_3$ | 1-Methyl-2-imidazolyl | H | 3 | — | 0 | 1 |
| N | S | H | H | H | $CH_3$ | 1,2,3-Triazol-4-yl | H | 3 | — | 0 | 1 |
| N | S | H | H | H | $CH_3$ | 1-Methyl-1,2,3-triazol-4-yl | H | 3 | — | 0 | 1 |
| N | S | H | H | H | $CH_3$ | 1,2,4-Triazol-3-yl | H | 3 | — | 0 | 1 |
| N | S | H | H | H | $CH_3$ | 4-Methyl-1,2,4-triazol-3-yl | H | 3 | — | 0 | 1 |
| N | S | H | H | H | $CH_3$ | Tetrazol-5-yl | H | 3 | — | 0 | 1 |
| N | S | H | H | H | $CH_3$ | 1-Methyltetrazol-5-yl | H | 3 | — | 0 | 1 |
| N | S | H | H | H | $CH_3$ | 1-(2-Dimethylaminoethyl)tetrazol-5-yl | H | 3 | — | 0 | 1 |
| N | S | H | H | H | $CH_3$ | 1-(2-Hydroxyethyl)tetrazol-5-yl | H | 3 | — | 0 | 1 |
| N | S | H | H | H | $CH_3$ | 1,2,3-Thiadiazol-4-yl | H | 3 | — | 0 | 1 |
| N | S | H | H | H | $CH_3$ | 1,3,4-Thiadiazol-2-yl | H | 3 | — | 0 | 1 |
| N | S | H | H | H | $CH_3$ | 5-Methyl-1,3,4-thiadiazol-2-yl | H | 3 | — | 0 | 1 |
| N | S | H | H | H | $CH_3$ | 2-Pyridinyl | H | 3 | — | 0 | 1 |
| N | S | H | H | H | $CH_3$ | 4-Pyridinyl | H | 3 | — | 0 | 1 |
| N | S | H | H | H | $CH_3$ | 2-Pyrimidinyl | H | 3 | — | 0 | 1 |
| N | S | H | H | H | $CH_3$ | 2-Benzimidazolyl | H | 3 | — | 0 | 1 |
| N | S | H | H | H | $CH_3$ | 2-Furanyl | H | 3 | — | 0 | 1 |
| N | S | H | H | H | $CH_3$ | 2-Thienyl | H | 3 | — | 0 | 1 |
| N | S | H | H | H | $CH_3$ | 5-Chloro-thiophen-2-yl | H | 3 | — | 0 | 1 |
| N | S | H | H | H | $CH_3$ | 5-(2-Dimethylaminomethyl)furan-2-yl | H | 3 | — | 0 | 1 |
| N | S | H | H | H | $CH_3$ | 5-Methyl-furan-2-yl | H | 3 | — | 0 | 1 |

TABLE 19

Compounds of the formula I (see attached formula sheet I)
where n = 0, p = 0, q = 0, R4 = H and
with the following further substituent meanings:

| X | Y | R1 | R2 | R3 | R5 | R6 | R7 | m | r | t | u |
|---|---|----|----|----|----|----|----|----|----|----|----|
| CH | $SO_2$ | H | H | H | $CH_3$ | Phenyl | H | 2 | 2 | 1 | 2 |
| CH | $SO_2$ | H | H | H | $CH_3$ | 3-Dimethylaminomethylphenyl | H | 2 | 2 | 1 | 2 |
| CH | $SO_2$ | H | H | H | $CH_3$ | 3-Piperidinomethylphenyl | H | 2 | 2 | 1 | 2 |
| CH | $SO_2$ | H | H | H | $CH_3$ | 2-Thiazolyl | H | 2 | 2 | 1 | 2 |
| CH | $SO_2$ | H | H | H | $CH_3$ | 4,5-Dimethyl-2-thiazolyl | H | 2 | 2 | 1 | 2 |
| CH | $SO_2$ | H | H | H | $CH_3$ | 2-Imidazolyl | H | 2 | 2 | 1 | 2 |
| CH | $SO_2$ | H | H | H | $CH_3$ | 1-Methyl-2-imidazolyl | H | 2 | 2 | 1 | 2 |
| CH | $SO_2$ | H | H | H | $CH_3$ | 1,2,3-Triazol-4-yl | H | 2 | 2 | 1 | 2 |
| CH | $SO_2$ | H | H | H | $CH_3$ | 1-Methyl-1,2,3-triazol-4-yl | H | 2 | 2 | 1 | 2 |
| CH | $SO_2$ | H | H | H | $CH_3$ | 1,2,4-Triazol-3-yl | H | 2 | 2 | 1 | 2 |
| CH | $SO_2$ | H | H | H | $CH_3$ | 4-Methyl-1,2,4-triazol-3-yl | H | 2 | 2 | 1 | 2 |
| CH | $SO_2$ | H | H | H | $CH_3$ | Tetrazol-5-yl | H | 2 | 2 | 1 | 2 |
| CH | $SO_2$ | H | H | H | $CH_3$ | 1-Methyltetrazol-5-yl | H | 2 | 2 | 1 | 2 |
| CH | $SO_2$ | H | H | H | $CH_3$ | 1-(2-Dimethylaminoethyl)tetrazol-5-yl | H | 2 | 2 | 1 | 2 |
| CH | $SO_2$ | H | H | H | $CH_3$ | 1-(2-Hydroxyethyl)tetrazol-5-yl | H | 2 | 2 | 1 | 2 |
| CH | $SO_2$ | H | H | H | $CH_3$ | 1,2,3-Thiadiazol-4-yl | H | 2 | 2 | 1 | 2 |
| CH | $SO_2$ | H | H | H | $CH_3$ | 1,3,4-Thiadiazol-2-yl | H | 2 | 2 | 1 | 2 |
| CH | $SO_2$ | H | H | H | $CH_3$ | 5-Methyl-1,3,4-thiadiazol-2-yl | H | 2 | 2 | 1 | 2 |
| CH | $SO_2$ | H | H | H | $CH_3$ | 2-Pyridinyl | H | 2 | 2 | 1 | 2 |
| CH | $SO_2$ | H | H | H | $CH_3$ | 4-Pyridinyl | H | 2 | 2 | 1 | 2 |
| CH | $SO_2$ | H | H | H | $CH_3$ | 2-Pyrimidinyl | H | 2 | 2 | 1 | 2 |
| CH | $SO_2$ | H | H | H | $CH_3$ | 2-Benzimidazolyl | H | 2 | 2 | 1 | 2 | and the salts of the compounds listed in the above tables.

The invention further relates to a process for the preparation of the compounds of the formula I and their salts.

The process comprises a) reacting mercaptobenzimidazoles of the formula II (see attached formula sheet I), in which X, R1, R2, R3 and R4 have the meanings indicated above, with picoline derivatives III (see attached formula sheet I), in which R5, R6, R7, Y, m, p, q, r, t and u have the meanings indicated above and A is a suitable leaving group, or b) reacting compounds of the formula IV (see attached formula sheet I), in which X, R1, R2, R3, R4, R5, R7, m, r and t have the meanings indicated above, n, p and q are the number 0 and A is a suitable leaving group, with compounds R6—$C_u$—$H_{2u}$—YH (where Y=S, O, NH or N-1-4C-alkyl), or c) reacting compounds of the formula V (see attached formula sheet II), in which X, R1, R2, R3, R4, R5, R7 and n have the meanings indicated above and Hal is a halogen atom, with thiols VI (see attached formula sheet II), in which R6, Y, m, q, r, t and u have the meanings indicated above, or d) reacting benzimidazoles of the formula VII (see attached formula sheet II), in which R1, R2, R3, R4 and X have the meanings indicated above and A is a suitable leaving group, with pyridines of the formula VIII (see attached formula sheet II), in which RS, R6, R7, Y, m, p, q, r, t and u have the meanings indicated above, and (if compounds of the formula I where n=1 or p=1 and/or q=1 or 2 and/or Y=SO or $SO_2$ are the desired final products), then oxidizing the compounds obtained where n=0 and/or p=0 and/or q=0 and/or Y=S, and/or converting the compounds obtained, if desired, subsequently into the salts and/or converting salts which are obtained, if desired, subsequently into the free compounds.

In the abovementioned reactions, the starting compounds can be employed as such or optionally in the form of their salts.

Suitable leaving groups A are, for example, halogen atoms, in particular chlorine, or hydroxyl groups activated by esterification (e.g. with p-toluenesulfonic acid).

The reaction of II with III is carried out in suitable, preferably polar, protic or aprotic solvents (such as methanol, ethanol, isopropanol, dimethyl sulfoxide, acetone, dimethylformamide or acetonitrile) with addition or with exclusion of water. It is carried out, for example, in the presence of a proton acceptor.

Those suitable are alkali metal hydroxides, such as sodium hydroxide, alkali metal carbonates, such as potassium carbonate, or tertiary amines, such as pyridine, triethylamine or ethyldiisopropylamine. Alternatively, the reaction can also be carried out without proton acceptors, it optionally first being possible —depending on the nature of the starting compounds —to separate off the acid addition salts in particularly pure form. The reaction temperature can be between 0° and 150° C., in the presence of proton acceptors temperatures between 20° and 80° C. and without proton acceptors between 60° and 120° C.—in particular the boiling temperature of the solvents used—being preferred. The reaction times are between 0.5 and 30— hours.

The reaction of the compounds IV with the compounds R6—$C_uH_{2u}$—YH is carried out in a similar manner to the reaction of the compounds II with the compounds III.

The reaction of the compounds V with the thiols VI is carried out in a manner known per se, such as is known to the person skilled in the art for the preparation of sulfides from thiols and halogenated aromatic compounds. The halogen atom Hal is preferably a chlorine atom.

The reaction of the compounds VII with the compounds VIII is carried out in principle analogously to the reaction of the compounds II with the compounds III.

The oxidation of the sulfides to the sulfoxides or sulfones is carried out under the conditions which are familiar to the person skilled in the art for the oxidation of sulfides to sulfoxides or sulfones [see for this, for example, J. Drabowicz and M. Mikolajczyk, Organic Preparations and Procedures Int. 14(1–2), 45–89(1982) or E. Block in S. Patai, The Chemistry of Functional Groups, Supplement E. Part 1, pp. 539–608, John Wiley and Sons (Interscience Publication), 1980]. Possible oxidants are all reagents customarily used for the oxidation of sulfides to sulfoxides or sulfones, in particular peroxy acids, such as, for example, peroxyacetic acid, trifluoroperoxyacetic acid, 3,5-dinitroperoxybenzoic acid, peroxymaleic acid, magnesium monoperoxyphthalate or preferably m-chloroperoxybenzoic acid.

The reaction temperature (depending on the reactivity of the oxidant and degree of dilution) is between −70° C. and the boiling temperature of the solvent used, but preferably between −30° and +20° C. Oxidation with halogens or with hypohalites (e.g. with aqueous sodium hypochlorite solution), which is expediently carried out at temperatures between 0° and 50° C., has also proven advantageous. The reaction is expediently carried out in inert solvents, e.g. aromatic or chlorinated hydrocarbons, such as benzene, toluene, dichloromethane or chloroform, preferably in esters or ethers, such as ethyl acetate, isopropyl acetate or dioxane, or in alcohols, preferably isopropanol.

The sulfoxides according to the invention are optically active compounds. Depending on the nature of the substituents, there can additionally be other chiral centers in the molecule. The invention therefore includes both the enantiomers and diastereomers and their mixtures and racemates. The enantiomers can be separated (see, for example, WO92/08716) in a manner known per se (for example by preparation and separation of corresponding diastereoisomeric compounds).

The compounds II are disclosed, for example, in WO86/02646, EP 134 400 or EP 127 763. The compounds III where p=0 and q=0 can be prepared, for example, as described in the following examples.

For compounds III where p=1 and q=1 or 2 and Y=SO or $SO_2$, the corresponding 2-hydroxymethyl-4-mercapto-substituted pyridines are oxidized, for example, using m-chloroperoxybenzoic acid and subsequently chlorinated, for example, using thionyl chloride. Reaction with 2-mercaptobenzimidazoles yields the compounds of the formula I where p=1 and q=1 or 2 and Y=SO or $SO_2$.

Depending on the nature of the substituent R6, the sulfoxides or sulfones are also obtained in the oxidation to give the sulfoxides n=1. Otherwise, the respective sulfides and sulfoxides or sulfones can be prepared by a choice of suitable starting compounds or by use of selective oxidants.

The starting compounds needed for the preparation of III can be prepared, for example, from the corresponding halogen compounds analogously to J. Med. Chem. 14 (1971) 349.

The compounds V, VI, VII and VIII are likewise known or they can be prepared analogously from known starting compounds by methods known per se. Thus, for example, compounds of the formula V are obtained by reaction of the compounds of the formula II with 4-halopyridines corresponding to compounds of the formula III.

The following examples explain the invention in greater detail, without restricting it. The compounds according to the invention and the starting compounds can be prepared in a manner analogous to that described in the examples.

EXAMPLES

Final Products 1. 2-{[3-Methyl-4-[2-phenoxy)ethylthio]-2-pyridinyl]methyllthio}-1 H-benzimidazole 2-{[[4-(2-Chloroethylthio]-3-methyl-2-pyridinyl]methyl]thio}-1 H-benzimidazole (10 mmol) is stirred at 100° C. in acetonitrile (25 ml) for 24 h with phenol (20 mmol) and potassium carbonate (60 mmol). After filtration, the filtrate is concentrated, and the product is taken up in dichloromethane, washed with 0.1N sodium hydroxide solution, dried over magnesium sulfate, concentrated and chromatographed on silica gel (EA/MeOH).

The title compound is obtained from the pure fractions after crystallization from diisopropyl ether in the form of colorless crystals; m.p. 72°–73° C.; yield: 64% of theory.

2. 2-([[3-Methyl-4-[(4-phenoxy)butylthiol-2-pyridinyl]methyl]thio}-1 H-benzimidazole According to the procedure described in Example 1, the title compound is obtained by reaction of 2-{[[4-(4-chlorobutylthio)-3-methyl-2-pyridinyl]methyl]-thio}-1 H-benzimidazole with phenol; m.p. 122°–123° C.; yield: 69% of theory.

3. 2-{[[3-Methyl-4-[5-(4-methylphenyl)-1,4-dithia-pent-1-yl]-2-pyridinyl]methyl]thio}-1 H-benzimidazole According to the procedure described in Example 1, the title compound is obtained by reaction of 2-{[[4-(2-chloroethylthio)-3-methyl-2-pyridinyl]methyl]-thio}-1 H-benzimidazole with 4-methylbenzylmercaptan after recrystallization from methanol/toluene; m.p. 129°–130° C; yield: 55% of theory.

4. 2-{[[4-[3-Dimethyldithiocarbamoylpropylthio]-3-methyl-2-pyridinyl]methyl]thio}1 H-benzimidazole According to the procedure described in Example 5, the title compound is obtained by reaction of 2-{[[4-(3-chloropropylthio)-3-methyl-2-pyridinyl]-methyl]thio}-1 H-benzimidazole in ethanol without addition of water with Na dimethylcarbamate as colorless crystals; m.p. 115°–117° C.; yield: 94% of theory.

5. 2-{[[4-[(6-Furan-2-yl)-1,5-dithiahex-1-yl]-3-methyl-2-pyridinyl]methyl]thio}-1 H-benzimidazole 2-}[[4-(3-Chloropropylthio)-3-methyl-2-pyridinyl] methyl]thio}-1 H-benzimidazole (3 mmol) is stirred under reflux with 2-furylmethylthiol (3.6 mmol) and 1N sodium hydroxide solution (4 ml) in ethanol (20 ml) for 20 h. After evaporating the ethanol in vacuo, 20 ml of water are added and the mixture is extracted with 3×10 ml of ethyl acetate. The combined organic phases are concentrated and the residue is chromatographed (EA/methanol/triethylamine). After crystallization from dichloromethane/diisopropyl ether, the title compound is obtained as a beige powder; m.p. 113°–116° C.; yield: 69% of theory.

6. 2-{[[4-[6-(2-Dimethylaminofuran-5-yl)-1,5-dithiahex-1-yl]-3-methyl-2-pyridinyl]methyl]thio}-1 H-benzimidazole trihydrochloride According to the procedure described in Example 5, the free title compound is obtained as an oil by reaction with 5-dimethylaminomethyl-2-furylmethylthiol. The title compound can be precipitated as the hydrochloride from acetone using gaseous hydrogen chloride; m.p. 112° C. (dec.).

7. 2-{[[3-Methyl-4-[7-(5-methylthiazol-4-yl)-1,5 dithiahept-1-yl]-2-pyridinyl]methyl]thio}-1 H-benzimidazole trihydrochloride According to the procedure described in Example 5, the title compound is obtained by reaction with 2-(5-methyl-4-thiazolyl)ethylthiol after precipitation with conc. hydrochloric acid in acetone; m.p. 159°–162° C.; yield: 83% of theory.

8. 2-{[[3-Methyl-4-[6-(2-guanidinothiazol-4-yl)-1.5 dithiahex-1-yl]-2-pyridinyl]methyl]thio}-1 H-benzimida-zole trihydrochloride According to the procedure described in 5, the title compound is obtained using 2-guanidinothiazol-4-methylthiol after precipitation with ethereal hydrochloric acid in acetone as a colorless, strongly hygroscopic powder; yield: 29% of theory; m.p. 185° C. (dec.).

9. 2-{[[3-Methyl-4-[5-(1 H-benzimidazol-2-yl)-1,5-dithiapent-1-yl]-2-pyridinyl]methyl]thio}-1 H-benzimidazole 2-{[[4-(3-Chloropropylthio)-3-methyl-2-pyridinyl] methyl]thio}-1 H-benzimidazole (1 mmol) is stirred at 60° C. for 20 h with 2-mercapto-1 H-benzimidazole (1.05 mmol) and 1N sodium hydroxide solution (3 ml) in 10 ml of ethanol and subsequently diluted with a further 10 ml of water. The mixture is allowed to cool, and the precipitated solid is filtered off, washed with ethanol/water 1/1 and dried in vacuo at 50° C. The title compound is obtained as a gray powder; m.p. 85°–87° C.; yield: 83% of theory.

10. 2-{[[4-[(5-Benzothiazol-2-yl)-1,5-dithiapent-1-yl]-3-methyl-2-pyridinyl]methyl]thio}-1 H-benzimidazole According to the procedure described in Example 9, the title compound is obtained by reaction with 2-mercaptobenzothiazole; m.p. 126°–128° C.; yield: 85% of theory.

11. 2-{[[4-[(5-Benzoxazol-2-yl)-1,5-dithiapent-1-yl]-3-methyl-2-pyridinyl]methyl]thio}1 H-benzimidazole According to the procedure described in Example 9, the title compound is obtained by reaction with 2-mercaptobenzoxazole; m.p. 73°–76° C.; yield: 72% of theory.

12. Sodium 2-{[5-[2-[1 H-benzimidazol-2-ylthio-methyl]-3-methyl-4-pyridinyl]-1,5-dithiapent-1-yl)}-pyridine-3-carboxylate 2-([[4-(3-Chloropropylthio)-3-methyl-2-pyridinyl] methyl]thio}-1 H-benzimidazole, methyl 2-mercaptonicotinate (1.2 equivalents) and calcium carbonate (5 equivalents) are heated to boiling under reflux in methanol for 20 h. After cooling, the mixture is filtered and concentrated to dryness, the product is treated with water and extracted with dichloromethane and residual dichloromethane is distilled off from the water phase. The solid precipitated from the water phase is filtered off with suction, washed with water and dried. The title compound is obtained; m.p. 129°–131° C.; yield: 47% of theory.

13. 2-{[[4-[3-(2-Carboxyphenylthio)propylthio]-3-methyl-2-pyridinyl]methyl]thio}-1 H-benzimidazole According to the procedure described in Example 12, the title compound is obtained by reaction with 2-mercaptobenzoic acid, after addition of aqueous hydrochloric acid to the water phase, as a beige solid; m.p. 142° C. (dec.); yield: 57% of theory.

14. 2-}[[3-Methyl-4-(3-pyridin-4-ylthio)propylthio)-2-pyridinyl]methyl]thio}-1 H-imidazo[4,5-b] pyridine 2-{[[4-(3-Chloropropylthio)-3-methyl-2-pyridinyl] methyl]thio}-1 H-imidazo[2,3-b]pyridine is warmed in ethanol/water 2:1 for 24 h with 4-mercaptopyridine (1.3 equivalents) and sodium hydroxide solution (2 equivalents). The mixture is diluted with water and allowed to cool. The precipitated solid is filtered off with suction and dried. The title compound is obtained; m.p. 69°–72° C.; yield: 39% of theory.

15. 2-{[[3-Methyl-4-(3-(1-methyltetrazol-5-ylthio)-propylthio)-2-pyridinyl]methyl]thio}-1 H-imidazo-[4,5-b]pyridine According to the precedure described in Example 14, the title compound is obtained by reaction with 1-methyl-2-mercaptotetrazole; m.p. 56° C. (dec.); yield: 78% of theory.

16. 2-{[[3-Methyl-4-(3-pyrimidin-2-ylthio)propylthio) -2-pyridinyl]methyl]thio}-1 H-imidazo-[4,5-b]pyridine According to the precedure described in Example 14, the title compound is obtained by reaction with 2-mercaptopyrimidine; m.p. 136° C. (dec.); yield: 90% of theory.

17. 2-{[[4-[3-(1-(2-Dimethylaminoethyl)tetrazol-5-yl-thio)propylthio]-2-pyridinyl]methyl]thio}-1 H-imidazo[4,5-b]pyridine trihydrochloride According to the procedure described in Example 14 the free base of the title compound is obtained by reaction with 1-[(2-dimethylamino)ethyl]-5-mercaptotetrazole as an oil. A hydrochloride is prepared from this using conc. hydrochloric acid in acetone and the title compound is obtained as a colorless solid; m.p. 81°–83° C.; yield: 39% of theory.

18. 2-{[[4-[5-(N-Cyano-N'-methylamidino)-1,5-dithiapent-1-yl]-3-methyl-2-pyridinyl]methyl]thio}-1 H-benzimidazole According to the procedure described in Example 5 the title compound is obtained directly by reaction with N-cyano-N'-methylisothiourea Na salt in isopropanol after addition of water to the reaction mixture as a pale yellow solid; m.p. 136°–138° C.; yield: 79% of theory.

19. 2-{4-[3-[5-Chlorothiophen-2-ylmethylthio)-propylthio]-3-methylpyridin-2-ylmethylthio}-1 H-benzimidazole 364 mg (1 mmol) of 2-}[[4-(3-chloropropylthio)-3-methyl-2-pyridinyl]methyl]thio}-1 H-benzimidazole, 340 mg (1.4 mmol) of 5-chloro-2-thiophen-2-ylmethylisothiuronium chlorine and 1.8 ml (3.5 mmol) of 2N NaOH are heated to reflux for 3 h in 10 ml of ethanol. The mixture is diluted with water and ethanol is distilled off. The residue is extracted 3 times with dichloromethane. The combined organic phases are washed with water, dried over magnesium sulfate, filtered and concentrated. The residue is chromatographed on silica gel using ethyl acetate/conc. ammonia=99/1. The title compound crystallizes on triturating with diisopropyl ether. M.p. 74°–77° C.; yield 240 mg (49% of theory).

20. 2-(3-Methyl-4-{3-[2-(2-methyl-5-nitroimidazol-1-yl)ethylthio]propylthio}pyridin-2-ylmethylthio) -1 H-benzimidazole trihydrochloride 4.3 g (12 mmol) of 2-[2-(2-methyl-5-nitroimidazol-1-yl)ethyl]isothiuronium iodide are dissolved in 80 ml of ethanol. 0.96 g (24 mmol) of sodium borohydride is added. After evolution of gas has ended, 2.9 g (8 mmol) of 2-{[[4-(3-chloropropylthio)-3-methyl-2-pyridinyl]methyl]thio}-1 H-benzimidazole are added. The mixture is stirred at RT for 8 h. After reaction has ended, it is acidified in order to destroy excess sodium borohydride. It is then diluted with water, ethanol is distilled off and the pH is adjusted to about 11. The mixture is extracted 3 times with dichloromethane. The combined organic phases are washed with water, dried over magnesium sulfate, filtered and concentrated. The residue is chromatographed on silica gel using ethyl acetate/methanol/conc. ammonia=89/10/1. The crude product is dissolved in isopropanol and acidified with conc. HCl. The mixture is completely concentrated. The title compound crystallizes on triturating with acetone. M.p. 144°–149° C.; yield 1.6 g (32% of theory).

21. 2-(3-Methyl-4-{3-[3-(2-methyl-5-nitroimidazol-1-yl)-propylthio]propylthio}pyridin-2-ylmethylthio) -1 H-benzimidazole dihydrochloride According to the procedure described in Example 20, the title compound is obtained by reaction with 2-[3-(2-methyl-5-nitroimidazol-1-yl)propyl]isothiuronium chlo-ride. M.p. 118° C. (dec.); yield 13% of theory.

22. 2-(3-Methyl-4-{2-[2-(2-methyl-5-nitroimidazol-1-yl)ethylthio]ethylthio}pyridin-2-ylmethylthio)-1 H-benzimidazole According to the procedure described in Example 19, the title compound is obtained by reaction of 2-{[[4-(2-chloroethylthio)-3-methyl-2-pyridinyl]methyl]-thio}-1 H-benzimidazole with 2-[2-(2-methyl-5-nitroimidazol-1-yl) -ethyl]isothiuronium iodide. M.p. 142°–145° C.; yield 33% of theory.

23. 2-(3-Methyl-4-{4-[2-(2-methyl-5-nitroimidazol-1-yl)ethylthio]butylthio}pyridin-2-ylmethylthio)-1 H-benzimidazole 2.5 g (6 mmol) of 2-chloromethyl-3-methyl-4-{4-[2-(2-methyl-5-nitroimidazol-1-yl)ethylthio]butylthio}-pyridine and 0.9 g (6 mmol) of 2-mercaptobenzimidazole are heated to reflux for 1 h in 25 ml of isopropanol. The mixture is then cooled in an ice bath and the precipitated solid is filtered off with suction. The solid is taken up in water and treated with saturated sodium hydrogen carbonate solution. The mixture is extracted with dichloromethane. The organic phase is washed with water, dried over magnesium sulfate, filtered and concentrated. The title compound crystallizes and is washed with a little methanol with stirring. M.p. 160°–162° C.; yield 0.62 g (20% of theory).

24. 2-(3-Methyl-4-{3-[2-(2-methyl-5-nitroimidazol-1-yl)ethylthio]propylthio}pyridin-2-ylmethylthio)-1 H-imidazo[4,5-b]pyridine 2.68 g (7.5 mmol) of 2-[2-(2-methyl-5-nitroimidazol-1-yl)ethyl]isothiuronium iodide are initially introduced in 30 ml of ethanol and treated with 0.57 g (15 mmol) of sodium borohydride. After evolution of gas has ended, 1.82 g (5 mmol) of 2-{[[4-(3-chloropropyithio)-3-methyl-2-pyridinyl]methyl]thio}-1 H-imidazo[4,5-b]pyridine are added. The mixture is heated to reflux for 10 h. After reaction has ended, it is acidified in order to destroy excess sodium borohydride. It is then diluted with water, ethanol is distilled off and the pH is adjusted to about 11. The mixture is extracted 3 times with dichloromethane. The combined organic phases are washed with water, dried over magnesium sulfate, filtered and concentrated. The residue is chromatographed on silica gel using ethyl acetate/methanol/conc. ammonia=75/20/5. The crude product is dissolved in isopropanol and acidified with conc. HCl. The solution is completely concentrated. The title compound crystallizes on triturating with acetone. M.p. 75° C. (dec.); yield 0.81 g (28% of theory).

Starting compounds

A1. 2-{[[4-(3-Chloropropylthio)-3-methyl-2-pyridinyl]-methyl]thio}-1 H-benzimidazole One equivalent of 2-chloromethyl-4-(3-chloropropylthio)-3-methylpyridine hydrochloride (dissolved in 10 ml of water) is added dropwise at 40° C. in the course of 20 min to a solution of 2-mercapto-1 H-benzimidazole (1.5 g/10 mmol) in 40 ml of ethanol and 21 ml of 1N sodium hydroxide solution. The mixture is then stirred for 2–3 h at 50°–60°C. and a further 3–4 h at room temperature, ethanol is distilled off on a rotary evaporator (1 kPa/40° C.), the residue is extracted 3 times with 20 ml of dichloromethane each time and the extracts are washed with 0.1N sodium hydroxide solution, dried over potassium carbonate and completely concentrated in vacuo. For purification, the crude product is chromatographed on silica gel (dichloromethane/methanol 20:1 to 3:1); the pure fractions collected are concentrated in vacuo together and crystallized from dichloromethane/diisopropyl ether. The product is then recrystallized from methanol/toluene.

Yield 2.67 g (74%) of the title compound as a colorless solid of m.p. 112°–114° C.

A2. 2-Chloromethyl-4-(3-chloropropylthio)-3-methylpyridine hydrochloride a) 2,3-Dimethyl-4-(3-hydroxypropylthio)pyridine-N-oxide 6 g (60%) NaH are added in portions to 50 ml of dry N-methylpyrrolidone (NMP), the mixture is stirred for 15 min, 9.5 g (0.11 mol) of 3-hydroxypropylmercaptan are metered in in the course of 20 min and the mixture is stirred again for 30 min until the evolution of gas has ended. A solution of 14.4 g (0.1 mol) of 4-chloro-2,3-dimethylpyridine-N-oxide in 100 ml of NMP is then added dropwise in the course of 20 min, and the reaction mixture is stirred for 1 h at room tempera- ture, then for 1 h at 70° C. and after this additionally for 1 h at 100° C.

After reaction has ended, the mixture is allowed to cool, and is diluted with 500 ml of water and extracted 4 times with 300 ml of dichloromethane each time. The combined organic phases are washed with water, dried over magnesium sulfate and concentrated and the residue is crystallized from toluene. After recrystallization from methanol/toluene, the title compound is obtained as a beige solid of m.p. 106°–107° C. (sublimes): yield: 68% of theory.

b) 2-Hydroxymethyl-4-(3-hvdroxypropylthio)-3-methylpyridine

The yellow oil obtained under a) is dissolved in 100 ml of acetic anhydride, and the mixture is stirred for 2 h at 100° C. After concentrating in vacuo, the brown, oily residue is distilled in a bulb tube distillation apparatus and reacted further without purification.

The oily distillate is heated to reflux temperature with stirring for 2 h in 100 ml of 2N sodium hydroxide solution and 100 ml of isopropanol, isopropanol is distilled off, the residue is extracted 3 times with 100 ml of dichloromethane each time, and the combined organic phases are washed with water, dried over potassium carbonate and concentrated in vacuo. 5.0 g of 2-hydroxymethyl-4-(3-hydroxypropylthio)-3-methylpyridine are obtained, which is reacted further without purification. A monohydrochloride of the title compound can be prepared from isopropanol using conc. hydrochloric acid; m.p. 188°–190° C. (dec.).

c) 2-Chloromethyl-4-(3-chlororopylthio)-3-methylpyridine hydrochloride 5.0 g of the oil from b) are dissolved in dichloromethane (100 ml), 4 equivalents of thionyl chloride are added dropwise and the mixture is stirred at room temperature for 20 h. It is completely concentrated and 4.5 g of the title compound are obtained as an oily, gradually crystallizing residue. Crystallization from isopropanol/diisopropyl ether yields the title compound as a colorless solid; m.p. 142°–144° C. (dec.).

B1. 2-{[[4-(2-Chloroethylthio)-3-methyl-2-pyridinyl]-methyl]thio}-1 H-benzimidazole According to the procedure given in Example A1, the title compound (62% of theory) is obtained by reaction of 2-mercapto-1 H-benzimidazole with 4-(2-chloroethylthio)-2-chloromethyl-3-methylpyridine hydrochloride and NaOH, after crystallization from ethyl acetate, as a colorless solid of m.p. 178°–180° C.

B2. 4-(2-Chloroethylthio)-2-chloromethyl-3-methylpyridine hydrochloride a) 2.3-Dimethyl-4-(2-hydroxyethylthio)pyridine-N-oxide According to the procedure given in Example A2.a), the title compound is obtained by reaction of 4-chloro-2,3-dimethylpyridine-N-oxide with 2-mercaptoethanol and sodium hydride as an oily residue which is employed in the subsequent step without further purification.

b) 4-(2-Hydroxyethylthio)-2-hydroxymethyl-3-methylpyridine

According to the procedure given in Example A2.b), the title compound is obtained by reaction of the oil obtained under a) with acetic anhydride and subsequent hydrolysis with NaOH as an oily residue which is employed in the subsequent step without further purification.

c) 4-(2-Chloroethylthio)-2-chloromethyl-3-methylpyridine hydrochloride

According to the procedure given in Example A2.c), the title compound is obtained by reaction of the oil obtained under b) with thionyl chloride as an oily residue which is employed directly as a solution in ethanol for the reaction with 2-mercaptobenzimidazole.

C. 3-Chloro-4-[N-(2-chloroethyl)-N-methylamino]-2-chloromethylpyridine hydrochloride a) 3-Chloro-4-[N-(2-hydroxyethyl)-N-methylamino]-2-hydroxymethylpyridine A mixture of 3,4-dichloro-2-hydroxymethylpyridine (J.Med.Chem. 1989, 32, 1970) (2.5 g) in 2-methylaminoethanol (30 ml) is heated at 160° C. for 2.5 h in a steel autoclave, the excess amine is stripped off under high vacuum and the residue which remains is chromatographed on silica gel (dichloromethane/methanol 95/S).

Yield: 2.3 g as a yellowish oil.

b) 3-Chloro-4-[N-(2-chloroethyl)-N-methylaminol-2-chloromethylpyridine hydrochloride A solution of 3-chloro-4-[N-(2-hydroxyethyl)-N-methylamino]-2-hydroxymethylpyridine (2.3 g) in dichloromethane (30 ml) is treated dropwise at 0° C. with a solution of thionyl chloride (4 ml) in dichloromethane (20 ml). The temperature is then allowed to rise to 20° C. (20 min) and the temperature is then kept at 40° C. for 30 min. After stripping off the solvent in vacuo, the residue which remains is chromatographed on silica gel (petroleum ether/ethyl acetate 7/3 mixture which contains 1 ml of conc. NH$_3$×aq/L) . Yield: 2.6 g.

D1. 2-{[[4-(3-Chloropropylthio)-3-methoxy-2-pyridin-yl]methyl]thio}-1 H-benzimidazole dihydrochloride 2-Mercapto-1 H-benzimidazole (10 g) and 2-chloromethyl-4-(3-chloropropylthio)-3-methoxypyridine hydrochloride (1 equivalent) are stirred at 80° C. for 5 h in 150 ml of isopropanol and 15 ml of water, the mixture is cooled, and precipitated solid is filtered off and recrystallized from isopropanol/water. The title compound is obtained as a light brown powder; m.p. 117°–119° C. (dec.); yield: 67% of theory.

D2. 2-Chloromethyl-4-(3-chlorpyropylthio)-3-methoxypyridine hydrochloride

According to the procedure described in Example A2 a, b, c, the title compound is obtained starting from 4-chloro-3-methoxy-2-methylpyridine-N-oxide as a slowly crystallizing oil which is directly reacted further.

E. 2-{[[4-(3-Chloropropylthio)-3-methyl-2-pyridinyl]-methyl]thio}-1 H-imidazo[4,5-b]pyridine dihydrochloride According to the procedure described in Example D1, the title compound is obtained in the reaction of 2-mercapto-1 H-imidazo[2,3-b]pyridine with 2-chloromethyl-4-(3-chloropropylthio)-3-methylpyridine hydrochloride as a colorless powder; m.p. 186°–188° C.; yield: 88% of theory.

F. 2-Chloromethyl-3-methyl-4-{4-[2-(2-methyl-5-nitroimidazol-1-yl)ethylthio]butylthio}pyridine a) 2-Hydroxymethyl-4-(4-mercaptobutylthio)-3-methylpyridine 4.2 g (145 mmol) of sodium hydride (80% in paraffin) are initially introduced in 100 ml of DMF with ice-cooling. 35.5 g (290 mmol) of 1,4-butanedithiol are slowly added drop-wise. After the evolution of gas has ended, 15.3 g (97 mmol) of 4-chloro-2-hydroxymethyl-3-methylpyridine in 20 ml of DMF are added drop-wise. After about 30 minutes, the mixture is allowed to come to RT and is stirred at this temperature for 12 h. It is diluted with 800 ml of ice-water and neutralized with acetic acid. The mixture is extracted 3 times with dichloromethane. The combined organic phases are washed 4 times with water, dried over magnesium sulfate, filtered and concentrated. The crude product is chromatographed on silica gel using ethyl acetate/conc. ammonia=99/1. The title compound is obtained as a yellow crystallizate. M.p. 58°–63° C.; yield 13 g (55% of theory).

b) 2-Hydroxymethyl-3-methyl-4-{4-[2-(2-methyl-5-nitroimidazol-1-yl)ethylthio]butylthio}pyridine 0.43 g (15 mmol) of sodium hydride are initially introduced in 25 ml of DMF with ice-cooling. 3.33 g (13.7 mmol) of 2-hydroxymethyl-4-(4-mercaptobutylthio)-3-methylpyridine are added. After the evolution of gas has ended, 2.62 g (13.7 mmol) of 1-(2-chloroethyl)-2-methyl-5-nitroimidazole in 10 ml of DMF are added dropwise. The mixture is stirred with ice- cooling for 1 h. It is then diluted with 200 ml of ice-water and neutralized with acetic acid. The mixture is extracted 3 times with dichloromethane. The combined organic phases are washed 4 times with water, dried over magnesium sulfate, filtered and concentrated. The crude product is chromatographed on silica gel using ethyl acetate/methanol/conc. ammonia=89/10/1. The title compound is obtained on concentrating as a yellow crystallizate which is washed by stirring with diethyl ether. M.p. 86°–87° C.; yield 4 g (75% of theory).

c) 2-Chloromethyl-3-methyl-4-{4-[2-(2-methyl-5-nitroimidazol- 1-yl)ethylthio]butylthio}pyridine 4 g (10 mmol) of 2-hydroxymethyl-3-methyl-4-{4-[2-(2-methyl-5-nitroimidazol-1-yl)ethylthio]butylthio}-pyridine are dissolved in 40 ml of dichloromethane. 1.56 g (13.11 mmol) of thionyl chloride in 5 ml of dichloromethane are added dropwise with ice-cooling. The mixture is stirred at 0C for 2 h. It is then added to 250 ml of ice-water and neutralized with saturated sodium hydrogen carbonate solution. The dichloromethane phase is separated off and the aqueous phase is extracted again with dichloromethane. The combined organic phases are washed with water, dried over magnesium sulfate, filtered and concentrated. The title compound is obtained as a yellow oil which is reacted without further purification. Yield 4.15 g (100% of theory).

COMMERCIAL UTILITY

The excellent activity of compounds of the formula I and their salts against Helicobacter bacteria allows their use in human medicine as active compounds for the treatment of diseases which are based on Helicobacter bacteria.

The invention thus further relates to a process for the treatment of mammals, especially humans, who are suffering from diseases which are based on Helicobacter bacteria.

The process comprises administering to the sick individual a therapeutically active and pharmacologically tolerable amount of one or more compounds of the formula I and/or their pharmacologically tolerable salts.

The invention additionally relates to the compounds of the formula I and their pharmacologically tolerable salts for use in the treatment of diseases which are based on Helicobacter bacteria.

The invention likewise comprises the use of compounds of the formula I and their pharmacologically tolerable salts in the production of medicaments which are employed for the control of those diseases which are based on Helicobacter bacteria.

The invention further relates to medicaments for the control of Helicobacter bacteria, which contain one or more compounds of the general formula I and/or their pharmacologically tolerable salts.

Of the Helicobacter strains against which the compounds of the formula I prove effective, the strain *Helicobacter pylori* may be mentioned in particular.

The medicaments are prepared by processes known per se, which are familiar to the person skilled in the art. As medicaments, the pharmacologically active compounds of the formula I and their salts (=active compounds) are either employed as such, or preferably in combination with suitable pharmaceutical auxiliaries, e.g. in the form of tablets, coated tablets, capsules, emulsions, suspensions, gels or solutions, the active compund content preferably being between 0.1 and 95%.

Auxiliaries which are suitable for the desired pharmaceutical formulations are familiar to the person skilled in the art on the basis of his expert knowledge. Besides solvents, gelling agents, tabletting auxiliaries and other active compound excipients, for example, antioxidants, dispersants, emulsifiers, antifoams, flavor corrigents, preservatives, solubilizers, colorants or permeation promoters and complexing agents (e.g. cyclodextrins) can be used.

The active compounds can, for example, be administered parenterally (e.g. intravenously) or in particular orally.

In general, in human medicine the active compounds are administered in a daily dose of approximately 0.2 to 50, preferably 1 to 30, mg/kg of body weight, if appropriate in the form of several, preferably 2 to 6, individual doses to achieve the desired result.

In this connection, as an essential aspect of the invention it is particularly to be mentioned that the compounds of the formula I in which n is the number 0 already prove to be active against Helicobacter bacteria on administration of those doses which are below the doses which would have to be employed to achieve an inhibition—adequate for therapeutic purposes—of gastric acid secretion.

Compounds of the formula I in which n is the number 1—besides their activity against Helicobacter bacteria—also have a pronounced gastric acid secretion-inhibiting action. Accordingly, these compounds can also be employed for the treatment of those diseases which are based on increased gastric acid secretion.

The compounds according to the invention can also be administered in a fixed or free combination together with a substance neutralizing gastric acid and/or inhibiting gastric acid secretion and/or with a substance suitable for the classical control of *Helicobacter pylori*.

Substances neutralizing gastric acid which may be mentioned are, for example, sodium hydrogen carbonate and other antacids (such as aluminum hydroxide, magnesium aluminate or magaldrate). Substances inhibiting gastric acid secretion which may be mentioned are, for example, $H_2$ blockers (e.g. cimetidine, ranitidine), $H^+/K^+$ ATPase inhibitors (e.g. lansoprazole, omeprazole or in particular pantoprazole) and also so-called peripheral anticholinergics (e.g. pirenzepine, telenzepine).

As substances suitable for the classical control of *Helicobacter pylori*, antimicrobially active substances may be mentioned in particular, such as, for example, penicillin G, gentamycin, erythromycin, nitrofurazone, tinidazole, nitrofurantoin, furazolidone, metronidazole and in particular amoxycillin, or else also bismuth salts such as, for example, bismuth citrate;

BIOLOGICAL INVESTIGATIONS

The compounds of the formula I were investigated regarding their activity against *Helicobacter pylori* following the methodology described by Tomoyuki Iwahi et al. (Antimicrobial Agents and Chemotherapy, 1991, 490–496) using Columbia agar (Oxoid) and with a growth period of 4 days. The approx. MIC 50 values listed in the following Table A resulted here for the compounds investigated (the numbers of the compounds given agree with the example numbers in the description).

TABLE A

| Compound No. | approx. MIC50 ($\mu$g/ml) |
| --- | --- |
| 1 | 0.05 |
| 2 | 0.1 |

TABLE A-continued

| Compound No. | approx. MIC50 ($\mu$g/ml) |
| --- | --- |
| 3 | 0.05 |
| 4 | 0.05 |
| 5 | 0.05 |
| 6 | 0.05 |
| 7 | 0.05 |
| 10 | 0.1 |
| 11 | 0.1 |
| 14 | 0.1 |

We claim:
1. A compound of the formula I

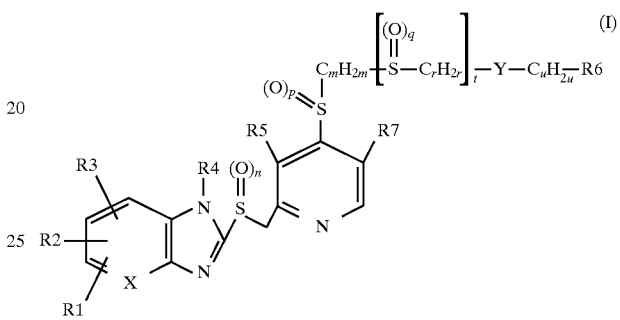

in which
X is CH or N,
Y is S, SO, $SO_2$, O, NH or N-1-4C-alkyl,
R1 is hydrogen, 1-4C-alkyl, 1-4C-alkoxy or halogen,
R2 is hydrogen, 1-4C-alkyl, 1-4C-alkoxy, halogen, trifluoromethyl, completely or predominantly fluorine-substituted 1-4C-alkoxy, chlorodifluoromethoxy, 2-chloro-1,1,2-trifluoroethoxy or in adjacent positions together with R3, completely or partially fluorine-substituted 1-2C-alkylenedioxy or chlorotrifluoroethylenedioxy,
R3 is hydrogen, completely or predominantly fluorine-substituted 1-4C-alkoxy, chlorodifluoromethoxy, 2-chloro-1,1,2-trifluoroethoxy or in adjacent positions together with R2, completely or partially fluorine-substituted 1-2C-alkylenedioxy or chlorotrifluoroethylenedioxy,
R4 is hydrogen, 1-4C-alkyl, R14-substituted 1-4C-alkyl, 1-4C-alkylcarbonyl, 2-4C-alkenylcarbonyl, halo-1-4C-alkylcarbonyl, N(R15)R16-1-4C-alkylcarbonyl, di-1-4C-alkylcarbamoyl or 1-4C-alkylsulfonyl,
R5 is hydrogen, 1-4C-alkyl or 1-4C-alkoxy,
R6 is a mono- or di-1-4C-alkylcarbamoyl or -thiocarbamoyl radical, an N-1-4C-alkyl-N'-cyanoamidino radical, a 1-N-1-4C-alkylamino-2-nitroethylene radical, an N-2-propynyl-N'-cyanoamidino radical, an aminosulfonylamidino radical, or an R8- and R9-substituted cyclic system or bicyclic system which is selected from the group consisting of benzene, furan, thiophene, pyrrole, oxazole, isoxazole, thiazole, thiazoline, isothiazole, imidazole, imidazoline, pyrazole, triazole, tetrazole, thiadiazole, thiadiazole-1-oxide, oxadiazole, pyridine, pyridine-N-oxide, pyrimidine, triazine, pyridone, benzimidazole, imidazopyridine, benzothiazole and benzoxazole,
R7 is hydrogen, 1-4C-alkyl or 1-4C-alkoxy,
R8 is hydrogen, 1-4C-alkyl, hydroxyl, 1-4C-alkoxy, halogen, nitro, guanidino, carboxyl, 1-4C- alkoxycarbonyl, R10-substituted 1-4C-alkyl or —N(R11)R12,

R9 is hydrogen, 1-4C-alkyl, hydroxyl, 1-4C-alkoxy, fluorine or trifluoromethyl,

R10 is hydroxyl, 1-4C-alkoxy, carboxyl, 1-4C-alkoxycarbonyl or —N(R11)R12, where R11 is hydrogen, 1-4C-alkyl or —CO-R13 and R12 is hydrogen or 1-4C-alkyl, or where R11 and R12, together and including the nitrogen atom to which both are bonded, are a piperidino or morpholino radical, R13 is hydrogen, 1-4C-alkyl or 1-4C-alkoxy, R14 is hydroxyl, 1-4C-alkoxy, carboxyl, 1-4C-alkoxycarbonyl or —N(R15)R16, where R15 is 1-4C-alkyl and R16 is 1-4C-alkyl, or where R15 and R16, together and including the nitrogen atom to which both are bonded, are a piperidino or morpholino radical, m is a number from 2 to 7, n is the number 0 or 1, p is the number 0 or 1, q is the number 0, 1 or 2, r is a number from 2 to 7, t is the number 0 or 1 and u is a number from 0 to 7 or a salt thereof, those compounds of the formula I being excluded in which Y is S or SO and, at the same time, X is CH, t is the number 0, u is the number 0, R4 is hydrogen or 1-4C-alkyl and R6 is an R8- and R9-substituted cyclic system or bicyclic system which is selected from the group consisting of benzene, furan, thiophene, pyrrole, oxazole, isoxazole, thiazole, thiazoline, isothiazole, imidazole, imidazoline, pyrazole, triazole, tetrazole, thiadiazole, oxadiazole, pyridine, pyridine-N-oxide, pyrimidine and benzimidazole, and furthermore those compounds of the formula I being excluded in which Y is NH or N-1-4C-alkyl and, at the same time, t is the number 0 and R5 is hydrogen or 1-4C-alkyl.

2. A compound of the formula I as claimed in claim 1, in which Y has the meaning O (oxygen).

3. A compound of the formula I as claimed in claim 1, in which X has the meaning CH, Y has the meaning S, t is the number 0 and u is a number from 1 to 7.

4. A compound of the formula I as claimed in claim 1, in which X has the meaning CH, Y has the meaning S, t is the number 0, u is the number 0 and R4 is R14-substituted 1-4C-alkyl, 1-4C-alkylcarbonyl, 2-4C-alkenylcarbonyl, halo-1-4C-alkylcarbonyl, N(R15)R16-1-4C-alkylcarbonyl, di-1-4C-alkylcarbamoyl or 1-4C-alkylsulfonyl.

5. A compound of the formula I as claimed in claim 1, in which Y has the meaning S, t is the number 0, u is the number 0 and R6 is a mono- or di-1-4C-alkylcarbamoyl or -thiocarbamoyl radical, an N-1-4C-alkyl-N'-cyanoamidino radical, a 1-N-1-4C-alkylamino-2-nitroethylene radical, an N-2-propynyl-N'-cyanoamidino radical, an aminosulfonylamidino radical, or an R8- and R9-substituted cyclic system which is selected from the group consisting of thiadiazole-1-oxide, triazine, pyridone, imidazopyridine, benzothiazole and benzoxazole.

6. A compound of the formula I as claimed in claim 1, in which Y is NH or N-1-4C-alkyl, t is the number 0 and R5 is 1-4C-alkoxy.

7. A compound of the formula I as claimed in claim 1, in which

X is CH or N,

Y is S or $SO_2$,

R1 is hydrogen, 1-4C-alkoxy or fluorine,

R2 is hydrogen, 1-4C-alkyl or fluorine,

R3 is hydrogen,

R4 is hydrogen, R14-substituted 1-4C-alkyl or 1-4C-alkylsulfonyl,

R5 is hydrogen or 1-4C-alkyl,

R6 is a di-1-4C-alkylthiocarbamoyl radical, an N-1-4C-alkyl-N'-cyanoamidino radical or an R8- and R9-substituted cyclic system which is selected from the group consisting of benzene, furan, thiophene, thiazole, imidazole, triazole, tetrazole, thiadiazole, pyridine, pyrimidine and triazine, R7 is hydrogen or 1-4C-alkyl, R8 is hydrogen, 1-4C-alkyl, hydroxyl, nitro, guanidino, carboxyl, 1-4C-alkoxycarbonyl or R10-substituted 1-4C-alkyl, R9 is hydrogen, 1-4C-alkyl, hydroxyl or fluorine, R10 is hydroxyl, 1-4C-alkoxycarbonyl or -N(R11)R12, where R11 is 1-4C-alkyl and R12 is 1-4C-alkyl, or where R11 and R12, together and including the nitrogen atom to which both are bonded, are a piperidino or morpholino radical, R14 is 1-4C-alkoxycarbonyl or —N(R15)R16, where R15 is 1-4C-alkyl and R16 is 1-4C-alkyl, or where R15 and R16, together and including the nitrogen atom to which both are bonded, are a piperidino or morpholino radical, m is a number from 2 to 4, n is the number 0, p is the number 0, t is the number 0 and u is a number from 0 to 3 and a salt thereof, those compounds of the formula I being excluded in which Y is S and, at the same time, X is CH, u is the number 0, R4 is hydrogen and R6 is an R8- and R9-substituted cyclic system which is selected from the group consisting of benzene, furan, thiophene, thiazole, imidazole, triazole, tetrazole, thiadiazole, pyridine and pyrimidine.

8. A compound of the formula I as claimed in claim 1, in which

X is CH or N,

Y is S or $SO_2$,

R1 is hydrogen, 1-4C-alkoxy or fluorine,

R2 is hydrogen or fluorine,

R3 is hydrogen,

R4 is hydrogen,

R5 is 1-4C-alkyl,

R6 is a di-1-4C-alkylthiocarbamoyl radical or an R8- and R9-substituted cyclic system which is selected from the group consisting of benzene, furan, thiophene, thiazole, imidazole, triazole, tetrazole, thiadiazole, pyridine and pyrimidine, R7 is hydrogen, R8 is hydrogen, nitro, 1-4C-alkoxycarbonyl or R10-substituted 1-2C-alkyl, R9 is hydrogen or 1-4C-alkyl, R10 is 1-4C-alkoxycarbonyl or —N(R11)R12, where R11 is 1-4C-alkyl and R12 is 1-4C-alkyl, or where R11 and R12, together and including the nitrogen atom to which both are bonded, are a piperidino or morpholino radical, m is the number 2 or 3, n is the number 0, p is the number 0, t is the number 0 and u is a number from 1 to 3 or a salt thereof.

9. A compound of the formula I as claimed in claim 1, in which

X is CH or N,

Y is S,

R1 is hydrogen,

R2 is hydrogen,

R3 is hydrogen,

R4 is hydrogen,

R5 is 1-4C-alkyl,

R6 is an R8- and R9-substituted cyclic system which is selected from the group consisting of benzene, furan, thiophene, thiazole, imidazole, triazole, tetrazole, thiadiazole, pyridine and pyrimidine, R7 is hydrogen, R8 is nitro, R9 is hydrogen or 1-4C-alkyl, m is the number 2 or 3, n is the number 0, p is the number 0, t is the number 0 and u is a number from 1 to 3 and their salts.

10. A compound of the formula I as claimed in claim 1, in which

X is CH or N,

Y is S,

R1 is hydrogen,

R2 is hydrogen,

R3 is hydrogen,

R4 is hydrogen,

R5 is 1-4C-alkyl,

R6 is R8- and R9-substituted imidazole,

R7 is hydrogen,

R8 is nitro,

R9 is hydrogen or 1-4C-alkyl, m is the number 2 or 3, n is the number 0, p is the number 0, t is the number 0 and u is a number from 1 to 3 or a salt thereof.

11. A compound of claim 1 wherein X is CH.

12. A compound of claim 1 wherein X is N.

13. The compound of claim 1 which is 2-(3-methyl-4-{3-[2-(2-methyl-5-nitroimidazol-1-yl)ethylthio]propylthio}pyridin-2-ylmethylthio)-1 H-benzimidazole or a salt thereof.

14. In a pharmaceutical composition comprising a suitable auxiliary and an effective amount of an active compound for treating a disease based on Helicobacter bacteria, the improvement wherein the active compound is a compound of claim 1 or a pharmaceutically-tolerable salt thereof.

15. A process for preparing a compound of formula I as claimed in claim 1 or a salt thereof, which comprises:

reacting a mercaptobenzimidazole of formula II (see attached formula sheet I), in which X, R1, R2, R3 and R4 have a meaning specified in claim 1, with a picoline derivative III (see attached formula sheet I), in which R5, R6, R7, y, m, p, q, r, t and u have a meaning specified in claim 1, and A is a suitable leaving group, and (when a compound of formula I where n=1 or p=1 and/or q=1 or 2 and/or Y=SO or $SO_2$ is a desired final product) oxidizing an obtained compound where n=O and/or p=O and/or q=O and/or Y=S, and optionally converting the obtained compound into a salt or converting an obtained salt into a free compound.

16. In a method for controlling Helicobacter bacteria by contacting such bacteria with a suitable compound, the improvement wherein the suitable compound is a compound of claim 1 or a salt thereof.

17. In a method for treating a mammal suffering from a disease based on Helicobacter bacteria by administering to the mammal an effective amount of an active ingredient, the improvement wherein the active ingredient is a compound of claim 1 or a pharmacologically-tolerable salt thereof.

18. In a process for compounding a medicament composition comprising a suitable auxiliary and an effective amount of active component for controlling Helicobacter bacteria, the improvement wherein the active component is a compound of claim 1 or a pharmacologically-tolerable salt thereof.

* * * * *